(12) United States Patent
Shimazaki

(10) Patent No.: US 11,312,728 B2
(45) Date of Patent: Apr. 26, 2022

(54) PROCESS FOR PREPARING 7H-PYRROLO[2,3-D]PYRIMIDINE DERIVATIVES AND CO-CRYSTALS THEREOF

(71) Applicant: Japan Tobacco Inc., Tokyo (JP)

(72) Inventor: Takahisa Shimazaki, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 16/470,843

(22) PCT Filed: Dec. 20, 2017

(86) PCT No.: PCT/JP2017/045728
§ 371 (c)(1),
(2) Date: Feb. 7, 2020

(87) PCT Pub. No.: WO2018/117151
PCT Pub. Date: Jun. 28, 2018

(65) Prior Publication Data
US 2020/0165269 A1 May 28, 2020

(30) Foreign Application Priority Data

Dec. 21, 2016 (JP) .............................. JP2016-247606

(51) Int. Cl.
*C07D 519/00* (2006.01)
*C07D 231/12* (2006.01)

(52) U.S. Cl.
CPC ......... *C07D 519/00* (2013.01); *C07D 231/12* (2013.01); *C07B 2200/13* (2013.01)

(58) Field of Classification Search
CPC .......................... C07B 2200/13; C07D 519/00
See application file for complete search history.

(56) References Cited

U.S. PATENT DOCUMENTS

2019/0062346 A1  2/2019  Yamasaki et al.

FOREIGN PATENT DOCUMENTS

| EP | 2460806 | 6/2012 |
|----|---------|--------|
| JP | WO 2011013785 | 2/2011 |
| JP | WO 2017006968 | 1/2017 |

OTHER PUBLICATIONS

Bhattacharya et al. (Brittain, ed. Polymorphism in Pharmaceutical Solids, 2009, p. 334.*
Stahly, G. Patrick (Crystal Growth & Design, 2009, vol. 9, pp. 4212-4299).*
Lopez et al., "Cocrystals of 3,5-Dimethyl-1 H-pyrazole and Salicylic Acid: Controlled Formation of Trimers via O—H—N Hydrogen Bonds", Crystal Growth and Design, 2007, 7(6):1176-1184.
PCT International Preliminary Report on Patentability in International Application No. PCT/JP2017/045728, dated Jun. 25, 2019, 11 pages.
PCT International Search Report and Written Opinion in International Application No. PCT/JP2017/045728, dated Feb. 27, 2018, 13 pages.
Extended European Search Report in EP Application No. 17883651.6, dated Apr. 17, 2020, 7 pages.
Foces-Foces et al., "Mixed Crystals of Pyrazoles and Benzoic Acids. Part 1. The Molecular Structure of 3,5-dimethylpyrazole-2,4,6-trimethylbenzoic Acid Co-Crystals", J. Chem. Soc., Perkin Trans. 2, pp. 349-353.
Yadav et al., "Co-Crystals: A Novel Approach to Modify Physiochemical Properties of Active Pharmaceutical Ingredients", Indian Journal of Pharmaceutical Sciences, Jul.-Aug. 2009, pp. 359-370.
Beckmann, "Seeding the Desired Polymorph: Background, Possibilities, Limitations and Base Studies", Organic Process Research and Development, 2000, 4:372-383.
Jones et al., "Pharmaceutical Cocrystals: An Emerging Approach to Physical Property Enhancement", MRS Bulletin, Nov. 2006, 31:875-879.

* cited by examiner

*Primary Examiner* — Susanna Moore
(74) *Attorney, Agent, or Firm* — Fish & Richardson P.C.

(57) ABSTRACT

The present invention relates to processes for preparing 7H-pyrrolo[2,3-d]pyrimidine derivatives which are useful as a Janus kinase (JAK) inhibitor, co-crystals thereof, processes for preparing the co-crystals, and processes for purifying 7H-pyrrolo[2,3-d]pyrimidine derivatives by employing the co-crystals. The present invention provides, for example, a process for preparing 3-[(3S,4R)-3-methyl-6-(7H-pyrrolo[2,3-d]pyrimidin-4-yl)-1,6-diazaspiro[3.4]octan-1-yl]-3-oxopropanenitrile by employing a co-crystal of 3-[(3S,4R)-3-methyl-6-(7H-pyrrolo[2,3-d]pyrimidin-4-yl)-1,6-diazaspiro[3.4]octan-1-yl]-3-oxopropanenitrile with 3,5-dimethylpyrazole.

16 Claims, 5 Drawing Sheets

US 11,312,728 B2

PROCESS FOR PREPARING 7H-PYRROLO[2,3-D]PYRIMIDINE DERIVATIVES AND CO-CRYSTALS THEREOF

CROSS-REFERENCE TO RELATED APPLICATIONS

This application is the U.S. National Stage of International Application No. PCT/JP2017/045728, filed on Dec. 20, 2017, which claims the benefit of Japanese Application No. 2016-247606, filed on Dec. 21, 2016. The contents of each of these applications are incorporated herein by reference in their entirety.

TECHNICAL FIELD

The present invention relates to process for preparing 7H-pyrrolo[2,3-d]pyrimidine derivatives which are useful as a Janus kinase (JAK) inhibitor, co-crystals thereof, process for preparing the co-crystals, and process for purifying 7H-pyrrolo[2,3-d]pyrimidine derivatives by employing the co-crystals.

JAK is a member of a cytoplasmic protein tyrosine kinase family, and for example, includes JAK1, JAK2, JAK3, and TYK2.

Patent Literature 1 discloses Compound A (3-[(3S,4R)-3-methyl-6-(7H-pyrrolo[2,3-d]pyrimidin-4-yl)-1,6-diazaspiro[3.4]octan-1-yl]-3-oxopropanenitrile: also referred to as Compound [4] hereinafter) which is useful as a JAK inhibitor.

CITATION LIST

Patent Literatures

[Patent Literature 1] WO 2011/013785 pamphlet

SUMMARY OF INVENTION

The present invention provides processes for preparing 7H-pyrrolo[2,3-d]pyrimidine derivatives which are useful as a JAK inhibitor, co-crystals thereof, processes for preparing the co-crystals, and processes for preparing or purifying 7H-pyrrolo[2,3-d]pyrimidine derivatives by employing the co-crystals.

The present invention includes the following embodiment:

A co-crystal of 3-[(3S,4R)-3-methyl-6-(7H-pyrrolo[2,3-d]pyrimidin-4-yl)-1,6-diazaspiro[3.4]octan-1-yl]-3-oxopropanenitrile with 3,5-dimethylpyrazole.

DESCRIPTION OF EMBODIMENTS

Figure 1:
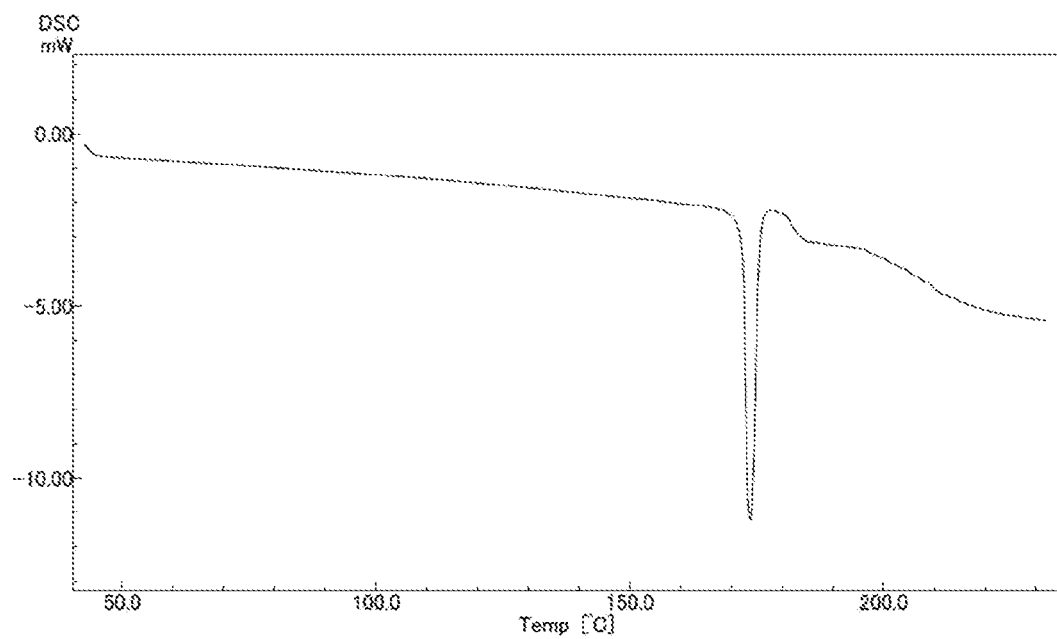
FIG. 1 shows a differential scanning calorimetry (DSC) curve for a co-crystal (Compound [3-1]) of Compound A (Compound [4]) with 3,5-dimethylpyrazole (2:1, molar ratio) as a seed crystal.

The definitions of the terms herein are as below.

In a process for preparing a compound of formula [4]

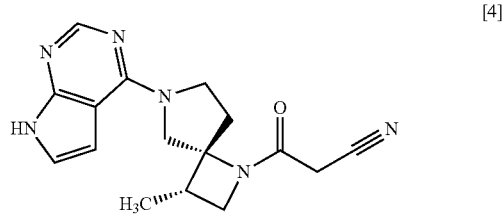

[4]

or its salt, the wording "employing a co-crystal of 3-[(3S,4R)-3-methyl-6-(7H-pyrrolo[2,3-d]pyrimidin-4-yl)-1,6-diazaspiro[3.4]octan-1-yl]-3-oxopropanenitrile with 3,5-dimethylpyrazole (e.g., Compound [3a])" denotes either of the following embodiments:

(1) Isolating a compound of formula [4] in the form of the co-crystal (e.g., Compound [3a]) from a reaction mixture; and (2) Adding a co-crystal (e.g., Compound [3a]), prepared in advance, as a seed crystal to a reaction mixture, followed by isolation of a compound of formula [4] in the form of the co-crystal (e.g., Compound [3a]) from the reaction mixture.

In the process for preparing a compound of formula [4] or its salt, a compound of formula [4] or its salt may be prepared from the co-crystal (e.g., Compound [3a]) isolated in the above (1) or (2).

In a process for purifying a compound of formula [4]

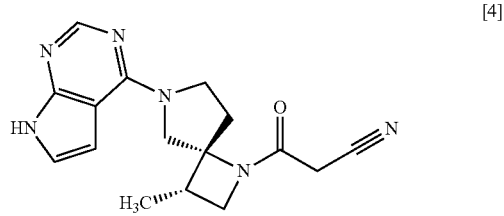 [SMILES: C[C@H]1CN(C(=O)CC#N)[C@]12CCN(c1ncnc3[nH]ccc13)C2]

[4]

or its salt, the wording "employing a co-crystal of 3-[(3S,4R)-3-methyl-6-(7H-pyrrolo[2,3-d]pyrimidin-4-yl)-1,6-diazaspiro[3.4]octan-1-yl]-3-oxopropanenitrile with 3,5-dimethylpyrazole (e.g., Compound [3a])" denotes either of the following embodiments:

(1) Isolating a compound of formula [4] in the form of the co-crystal (e.g., Compound [3a]) from a reaction mixture;

(2) Converting a crude product of a compound of formula [4] or its salt into a co-crystal (e.g., Compound [3a]), followed by isolation of a compound of formula [4] in the form of the co-crystal (e.g., Compound [3a]);

(3) Adding a co-crystal (e.g., Compound [3a]), prepared in advance, as a seed crystal to a reaction mixture, followed by isolation of a compound of formula [4] in the form of the co-crystal (e.g., Compound [3a]) from the reaction mixture; and
(4) Converting a crude product of a compound of formula [4] or its salt into a co-crystal (e.g., Compound [3a]) with addition of a co-crystal (e.g., Compound [3a]), prepared in advance, as a seed crystal, followed by isolation of a compound of formula [4] in the form of the co-crystal (e.g., Compound [3a]).

In the process for purifying a compound of formula [4] or its salt, a purified compound of formula [4] or its salt may be prepared via a step comprising crystallization after dissolving the co-crystal (e.g., Compound [3a]) isolated in any one of the above (1) to (4).

For example, a compound of formula [4] herein may be also referred to as Compound [4].

Salts of compounds may be any salts if such salts can be formed with the compound of the present invention, and includes, for example, salts with inorganic acids, salts with organic acids, salts with inorganic bases, salts with organic bases, salts with amino acids.

The inorganic acids include, for example, hydrochloric acid, nitric acid, sulfuric acid, phosphoric acid, hydrobromic acid.

The organic acids include, for example, oxalic acid, malonic acid, maleic acid, citric acid, fumaric acid, terephthalic acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid, 10-camphorsulfonic acid.

The salts with inorganic bases include, for example, sodium salt, potassium salt, calcium salt, magnesium salt, ammonium salt.

The organic bases include, for example, methylamine, diethylamine, trimethylamine, triethylamine, ethanolamine, diethanolamine, triethanolamine, ethylenediamine, tris(hydroxymethyl)methylamine, dicyclohexylamine, N,N-dibenzylethylenediamine, guanidine, pyridine, picoline, choline, cinchonine, meglumine.

The amino acids include, for example, lysine, arginine, aspartic acid, glutamic acid.

According to known methods, the compound of the present invention may be reacted with inorganic bases, organic bases, inorganic acids, organic acids, or amino acids to give salts of the compound of the present invention.

The compound or its salt of the present invention may exist as its solvate.

The solvate is a compound where a molecule of a solvent coordinates to the compound or its salt of the present invention, and includes a hydrate. The preferable solvate is a pharmaceutically acceptable solvate, and includes, for example, a hydrate, an ethanolate, a solvate with DMSO, a 1-propanolate, a 2-propanolate, a solvate with chloroform, a solvate with dioxane, a solvate with anisole, a solvate with acetone, a solvate with ethyleneglycol, or a solvate with dimethylacetamide of the compound or its salt of the present invention.

According to known methods, a solvate of the compound or its salt of the present invention may be obtained.

The compound of the present invention may exist as a tautomer. In such case, the compound of the present invention may exist as a single tautomer or a mixture of individual tautomers.

The compound of the present invention may have a carbon-carbon double bond. In such case, the compound of the present invention may exist as E form, Z form, or a mixture of E form and Z form.

The compound of the present invention may exist as a stereoisomer to be identified as a cis/trans isomer. In such case, the compound of the present invention may exist as a cis form, trans form, or a mixture of a cis form and a trans form.

The compound of the present invention may have one or more asymmetric carbon atoms. In such case, the compound of the present invention may exist as a single enantiomer, a single diastereomer, a mixture of enantiomers, or a mixture of diastereomers.

The compound of the present invention may exist as an atropisomer. In such case, the compound of the present invention may exist as a single atropisomer, or a mixture of individual atropisomers.

The compound of the present invention may simultaneously include several structural features causing the above isomers. The compound of the present invention may include the above isomers in any ratios.

In the absence of other references such as annotation and the like, the formulae, chemical structures and compound names indicated in the present specification without specifying the stereochemistry thereof encompass all the above-mentioned isomers that may exist.

The chemical bond shown in a wavy line represents that the compound is a mixture of stereoisomers or any of stereoisomers. For example, a compound of formula [10]:

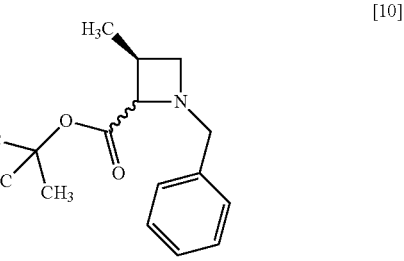

represents a mixture of formulae [10-1] and [10-2]:

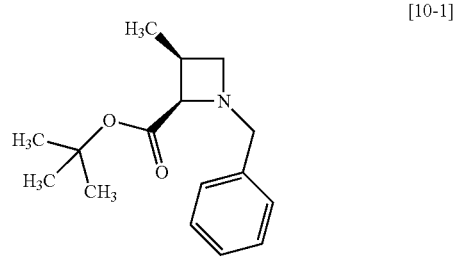

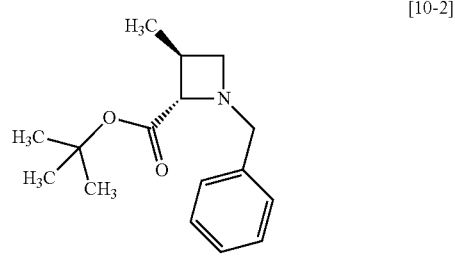 [SMILES: C[C@H]1CN(Cc2ccccc2)C1C(=O)OC(C)(C)C ; Cl]

or any one of the compounds.

A diasteromeric mixture may be separated into each diastereomer by a conventional method such as chromatography or crystallization. Each diastereomer may be also obtained by using a stereochemically single starting material or by a synthetic method using a stereoselective reaction.

A separation of enantiomeric mixture into each single enantiomer may be carried out by well-known methods in the field.

For example, according to a standard method such as fractional crystallization or chromatography, a diastereomer with a higher isomeric ratio or a substantially pure single diastereomer may be separated from a diastereomeric mixture which is formed by reacting an enantiomeric mixture with a chiral auxiliary which is a substantially pure enantiomer. The separated diastereomer may be converted into the desired enantiomer by removing off the added chiral auxiliary in a cleavage reaction.

The desired enantiomer may be also obtained by directly separating an enantiomeric mixture by a chromatography using a chiral solid phase well known in the field.

Alternatively, the desired enantiomer may be also obtained by using a substantially pure optically active starting material or by a stereoselective synthesis using a chiral auxiliary or asymmetric catalyst to a prochiral synthetic intermediate, i.e. asymmetric induction.

An absolute configuration may be determined by X-ray crystal analysis of a crystalline final product or synthetic intermediate. If necessary, an absolute configuration may be determined by using a crystalline final product or synthetic intermediate derivatized with a reagent having an asymmetric center of which a steric configuration is known. The configuration herein was specified by X-ray crystal analysis of a crystalline chloroformate of Compound [4].

The compound of the present invention may be crystalline or amorphous.

The compound of the present invention may be labelled with an isotope including $^3H$, $^{14}C$, $^{35}S$.

A co-crystal of 3-[(3S,4R)-3-methyl-6-(7H-pyrrolo[2,3-d]pyrimidin-4-yl)-1,6-diazaspiro[3.4]octan-1-yl]-3-oxopropanenitrile with 3,5-dimethylpyrazole in the present invention is preferably a co-crystal of 3-[(3S,4R)-3-methyl-6-(7H-pyrrolo[2,3-d]pyrimidin-4-yl)-1,6-diazaspiro[3.4]octan-1-yl]-3-oxopropanenitrile with 3,5-dimethylpyrazole with a molar ratio ranging from 2:0.8 to 2:1. A more preferable molar ratio is 2:1.

A co-crystal of formula [3a]

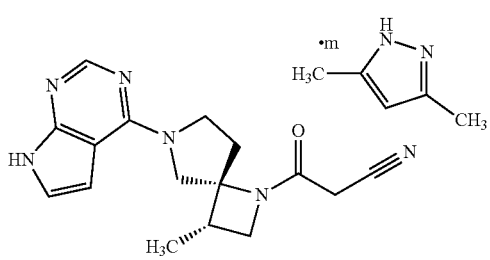

[3a]

wherein m is any number of 0.4 to 0.5 in the present invention is preferably a co-crystal wherein m is 0.5.

In another preferable embodiment, a co-crystal of formula [3a] is a co-crystal wherein m is 0.40 to 0.48, 0.40 to 0.46, 0.40 to 0.44, 0.40 to 0.42, 0.42 to 0.50, 0.44 to 0.50, 0.46 to 0.50, 0.48 to 0.50, 0.42 to 0.44, 0.44 to 0.46, or 0.46 to 0.48.

A compound of formula [4]

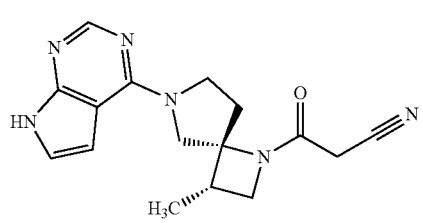

[4]

or its salt in the present invention is preferably a free form of the compound of formula [4].

Processes for preparing the co-crystal in the present invention, or the compound or its salt in the present invention or a solvate thereof is illustrated as below.

In each step, the reaction may be carried out in a solvent.

The compound obtained in each step may be isolated and purified by a known method such as distillation, recrystallization, column chromatography, if needed, or may be optionally used in a subsequent step without isolation or purification.

The room temperature herein represents a condition wherein a temperature is not controlled, and includes 1° C. to 40° C. as one embodiment. The reaction temperature may include the temperature as described ±5° C., preferably ±2° C.

An example of a process for preparing the co-crystal in the present invention, or the compound or its salt in the present invention or a solvate thereof is shown in the following Scheme. Specifically, a scheme via compound [3a] is shown.

In the scheme, m is any number of 0.4 to 0.5.

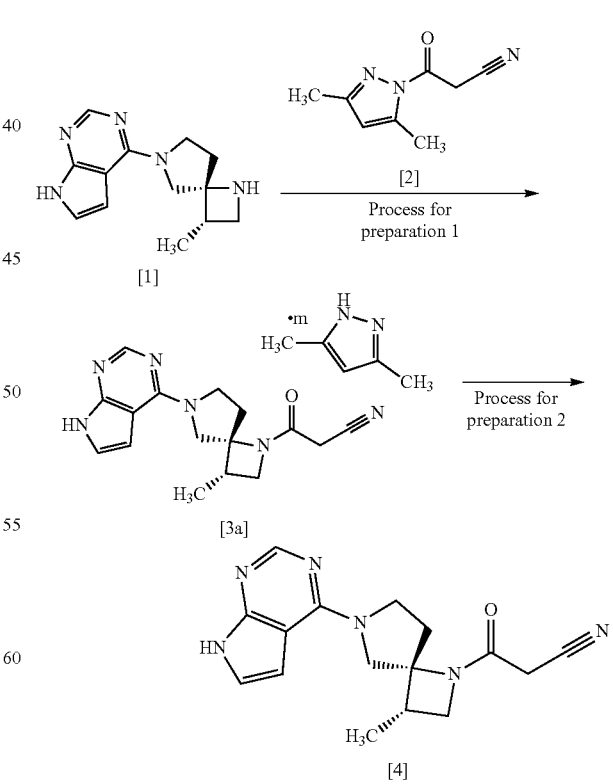

Below are detailed explanations of the processes shown in the above scheme.

[Process for Preparation 1] Preparation of a Co-Crystal of Formula [3a]

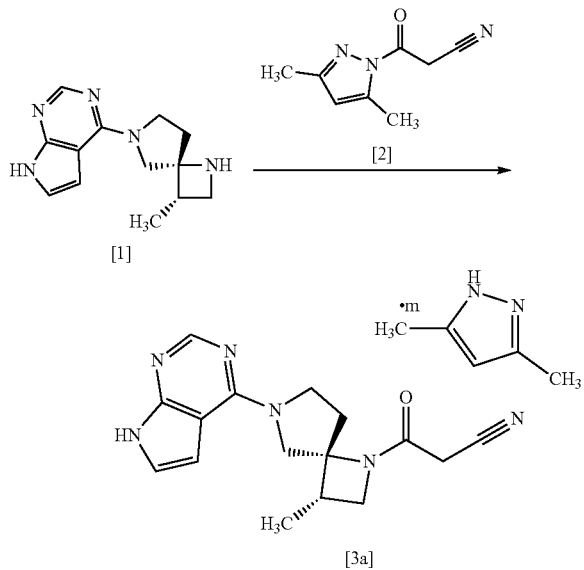

In the scheme, m is any number of 0.4 to 0.5.

A co-crystal of formula [3a] may be prepared by condensing a compound of formula [1] with 1-cyanoacetyl-3,5-dimethyl-1H-pyrazole (DPCN) [2]. The compound of formula [1] may be in its salt form, and the formation of a salt from the free form or the formation of the free form from a salt can be performed according to any procedures known in the art.

A preferable solvent is acetonitrile.

DPCN [2] may be used, for example, in an amount of 0.95 to 1.2 equivalents relative to the compound of formula [1], preferably 1.1±0.05 equivalents. Another preferable embodiment is 1.0±0.05 equivalents.

The reaction temperature is in the range of, for example, room temperature to 80° C., preferably 70° C. to 80° C.

The reaction time is, for example, between 0.5 hr and 12 hr, preferably between 0.5 hr and 6 hr.

The symbol "m" of the co-crystal of formula [3a] may be any of numbers from 0.4 to 0.5 depending on reaction, filtration of co-crystals, or drying conditions.

The compound of formula [3a] may be, for example, the crystal showing the X-ray powder diffraction pattern having at least one (for example, at least 1, 2 or 3) peak at 4.6°±0.2°, 18.6°±0.2° or 20.9°±0.2° of the diffraction angle (2θ) measured by using CuKα radiation.

Preferably, the compound of formula [3a] may be the crystal showing the X-ray powder diffraction pattern having at least one (for example, at least 1, 2 or 3) peak at 4.6°±0.1°, 18.6°±0.1° or 20.9°±0.1° of the diffraction angle (2θ) measured by using CuKα radiation.

More preferably, the compound of formula [3a] may be the crystal showing the X-ray powder diffraction pattern having at least one (for example, at least 1, 2 or 3) peak at 4.6°±0.06°, 18.6°±0.06° or 20.9°±0.06° of the diffraction angle (2θ) measured by using CuKα radiation.

Further, the compound of formula [3a] may also be, for example, the crystal showing the X-ray powder diffraction pattern having at least one (for example, at least 1, 2, 3, 4, or 5) peak at 4.6°±0.2°, 12.6°±0.2°, 16.1°±0.2°, 18.6°±0.2° or 20.9°±0.2° of the diffraction angle (2θ) measured by using CuKα radiation.

Preferably, the compound of formula [3a] may also be the crystal showing the X-ray powder diffraction pattern having at least one (for example, at least 1, 2, 3, 4, or 5) peak at 4.6°±0.1°, 12.6°±0.1°, 16.1°±0.1°, 18.6°±0.1° or 20.9°±0.1° of the diffraction angle (2θ) measured by using CuKα radiation.

More preferably, the compound of formula [3a] may also be the crystal showing the X-ray powder diffraction pattern having at least one (for example, at least 1, 2, 3, 4, or 5) peak at 4.6°±0.06°, 12.6°±0.06°, 16.1°±0.06°, 18.6°±0.06° or 20.9°±0.06° of the diffraction angle (2θ) measured by using CuKα radiation.

A co-crystal of formula [3a] is a co-crystal showing an extrapolated onset temperature of 172±5° C. in differential scanning calorimetry.

A preferable co-crystal of formula [3a] is a co-crystal showing an extrapolated onset temperature of 172±3° C. in differential scanning calorimetry.

A more preferable co-crystal of formula [3a] is a co-crystal showing an extrapolated onset temperature of 172±1° C. in differential scanning calorimetry.

A co-crystal of formula [3a] is a co-crystal showing an endothermic peak of 173±5° C. in differential scanning calorimetry.

A preferable co-crystal of formula [3a] is a co-crystal showing an endothermic peak of 173±3° C. in differential scanning calorimetry.

A more preferable co-crystal of formula [3a] is a co-crystal showing an endothermic peak of 173±1° C. in differential scanning calorimetry.

[Process for preparation 2] Preparation (Purification) of a compound of formula [4]

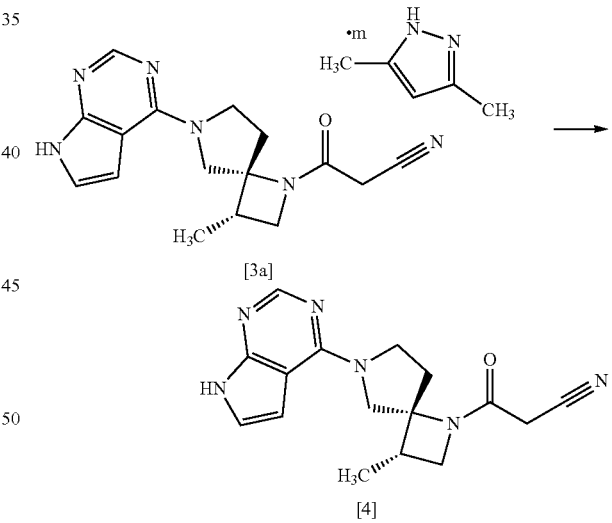

In the scheme, m has the same meaning as defined above.

The compound of formula [4] may be prepared by crystallization after dissolving the compound of formula [3a]. The preparation (purification) may be performed by the addition of 2,6-di-tert-butyl-4-methylphenol (BHT) during the crystallization.

Examples of the solvent for crystallization include, for example, 1-butanol and 1-propanol. A preferable solvent is 1-butanol. The solvent may be used, for example, in an amount of from 8.0 folds to 20 folds relative to the weight of the compound of formula [3a], preferably 8.5 folds±0.5 folds.

The temperature for dissolving the compound [3a] into the solvent for crystallization is in the range of, for example, 100° C. to 117° C., preferably 110° C.±5° C.

The time for crystallization is, for example, between 15 hr and 48 hr, preferably between 18 hr and 24 hr.

The process for preparing the co-crystal in the present invention, or the compound or its salt in the present invention or a solvate thereof may, for example, have the following advantage over the Preparation 6 in Patent Literature 1:

(1) Procedures for isolation and purification by extraction and silica gel column chromatography can be unnecessary by virtue of a highly stable co-crystal which can be directly isolated from a reaction mixture. Compound A (compound [4]) can be prepared with a chemically high purity.

Embodiments of the present invention include the following embodiments:

Item 1: A co-crystal of 3-[(3S,4R)-3-methyl-6-(7H-pyrrolo[2,3-d]pyrimidin-4-yl)-1,6-diazaspiro[3.4]octan-1-yl]-3-oxopropanenitrile with 3,5-dimethylpyrazole.

Item 2: The co-crystal of Item 1, having the structure of formula [3a]

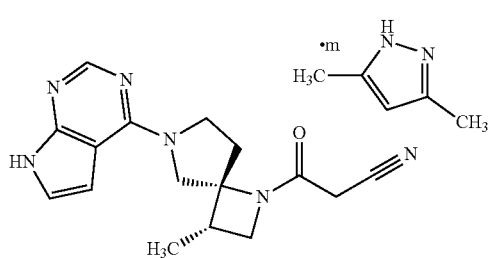

[3a]

wherein m is any number of 0.4 to 0.5.

Item 3: The co-crystal of Item 2, wherein m is 0.5.

Item 4: The co-crystal of any one of Items 1 to 3, showing an extrapolated onset temperature of 172±5° C. in differential scanning calorimetry.

Item 5: The co-crystal of any one of Items 1 to 4, showing a X-ray powder diffraction pattern having at least one peak at 4.6°±0.2°, 18.6°±0.2° or 20.9°±0.2° of a diffraction angle (2θ) measured by using CuKα radiation.

Item 6: The co-crystal of any one of Items 1 to 4, showing a X-ray powder diffraction pattern having at least one peak at 4.6°±0.2°, 12.6°±0.2°, 16.1°±0.2°, 18.6°±0.2° or 20.9°±0.2° of a diffraction angle (2θ) measured by using CuKα radiation.

Item 7: A process for preparing a compound of formula [4]

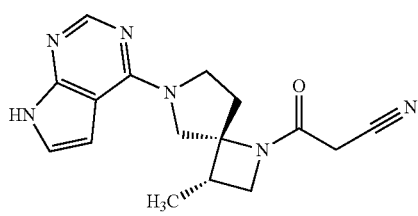

[4]

or its salt by employing the co-crystal of any one of Items 1 to 6.

Item 8: The process of Item 7, further comprising the step of reacting a compound of formula [1]

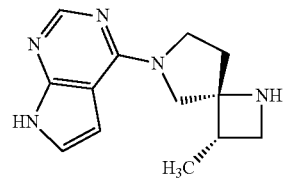

[1]

or its salt with a compound of formula [2]

[2]

to give a compound of formula [4] or its salt.

Item 9: A process for purifying a compound of formula [4]

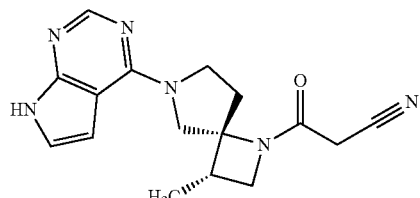

[4]

or its salt by employing the co-crystal of any one of Items 1 to 6.

Item 10: The process of Item 9, further comprising the step of reacting a compound of formula [1]

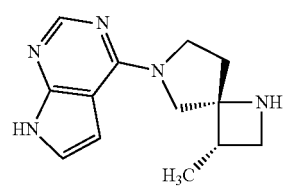

[1]

or its salt with a compound of formula [2]

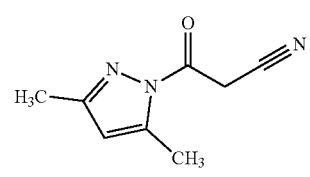

[2]

to give a compound of formula [4] or its salt.

Item 11: A process for preparing a co-crystal having the structure of formula [3a]

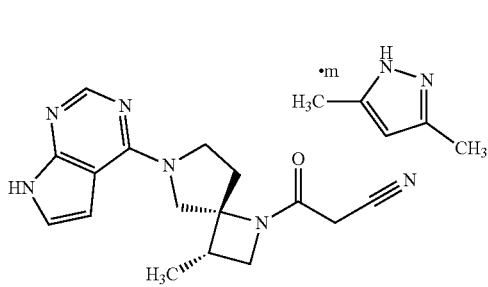

[3a]

wherein m is any number of 0.4 to 0.5, comprising the step of reacting a compound of formula [1]

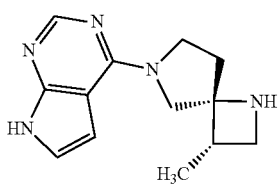

[1]

or its salt with a compound of formula [2]

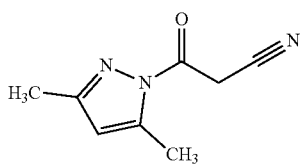

[2]

to give the co-crystal of formula [3a].

Item 12: A process for preparing a co-crystal having the structure of formula [3a]

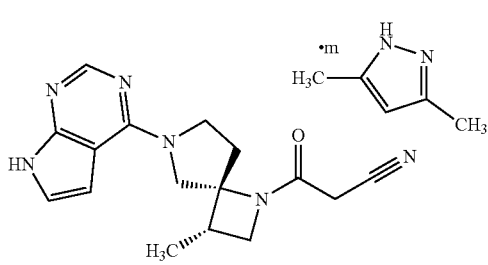

[3a]

wherein m is any number of 0.4 to 0.5, comprising the step of reacting a compound of formula [4]

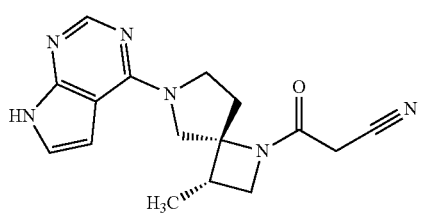

[4]

or its salt with a compound of formula [5]

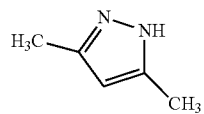

[5]

to give the co-crystal of formula [3a].

Item 13: The process of Item 11 or 12, wherein m is 0.5.

Item 14: The process of any one of Items 11 to 13, wherein the co-crystal of formula [3a] shows an extrapolated onset temperature of 172±5° C. in differential scanning calorimetry.

Item 15: The process of any one of Items 11 to 14, wherein the co-crystal of formula [3a] shows a X-ray powder diffraction pattern having at least one peak at 4.6°±0.2°, 18.6°±0.2° or 20.9°±0.2° of a diffraction angle (2θ) measured by using CuKα radiation.

Item 16: The process of any one of Items 11 to 14, wherein the co-crystal of formula [3a] shows a X-ray powder diffraction pattern having at least one peak at 4.6°±0.2°, 12.6°±0.2°, 16.1°±0.2°, 18.6°±0.2° or 20.9°±0.2° of a diffraction angle (2θ) measured by using CuKα radiation.

Item 17: A compound of formula [4]

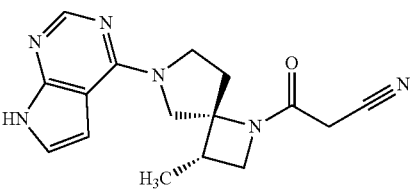

[4]

or its salt, which is prepared or may be prepared by the process of Item 7 or 8.

Item 18: A co-crystal of formula [3a]

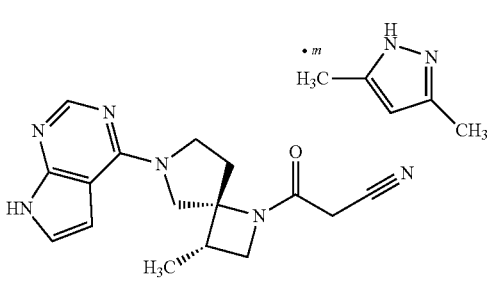

[3a]

wherein m is any number of 0.4 to 0.5, which is prepared or may be prepared by the process of Item 11 or 12.

Item 19: The co-crystal of Item 18, wherein m is 0.5.

EXAMPLES

Specific processes for preparing a co-crystal in the present invention, or a compound or its salt in the present invention or a solvate thereof are illustrated as examples hereinafter. However, the present invention is not restricted by these Examples.

In the crystallization steps in the preparation (purification) of Compound A (Compound [4]) (Example 3), the preparation of Compound [6] (Example 4 Step 4), and the preparation of Compound [20] (Example 14), seed crystals were used to facilitate the crystallization. The crystals of these compounds can be obtained according to the methods described in the Examples even without employing seed crystals.

The meanings of the abbreviations used in the specification are shown below.

SR-MDOP: 4-[(3S,4R)-3-methyl-1,6-diazaspiro[3.4]-octan-6-yl]-7H-pyrrolo[2,3-d]pyrimidine Compound A (Compound [4]): 3-[(3S,4R)-3-methyl-6-(7H-pyrrolo[2,3-d]pyrimidine-4-yl)-1,6-diazaspiro[3.4]octan-1-yl]-3-oxopropanenitrile S-BAPO: (S)-2-(benzylamino) propan-1-ol S-BBMO: tert-butyl (S)—N-benzyl-N-(1-hydroxypropan-2-yl)glycinate R-BCAB: tert-butyl (R)—N-benzyl-N-(2-chloropropyl)glycinate S-MABB: tert-butyl (3S)-1-benzyl-3-methylazetidine-2-carboxylate S-MABB-HC: tert-butyl (3S)-1-benzyl-3-methylazetidine-2-carboxylate hydrochloride S-MACB-HC: tert-butyl (3S)-3-methylazetidine-2-carboxylate hydrochloride S-ZMAB: 1-benzyl 2-(tert-butyl) (3S)-3-methylazetidine-1,2-dicarboxylate RS-ZMBB: 1-benzyl 2-(tert-butyl) (2R,3S)-2-(2-(tert-butoxy)-2-oxoethyl)-3-methylazetidine-1,2-dicarboxylate RS-ZMAA: (2R,3S)-1-((benzyloxy)carbonyl)-2-(carboxymethyl)-3-methylazetidine-2-carboxylic acid RS-ZMAA-DN.2H$_2$O: disodium (2R,3S)-1-((benzyloxy)carbonyl)-2-(carboxymethyl)-3-methylazetidine-2-carboxylate di-hydrate RS-ZMOO: benzyl (2R,3S)-2-(2-hydroxyethyl)-2-(hydroxymethyl)-3-methylazetidine-1-carboxylate RS-ZMSS: benzyl (2R,3S)-3-methyl-2-(2-((methylsulfonyl)oxy)ethyl)-2-(((methylsulfonyl)oxy)methyl)azetidine-1-carboxylate SR-ZMDB: benzyl (3S,4R)-6-benzyl-3-methyl-1,6-diazaspiro[3.4]octane-1-carboxylate SR-MDOZ: benzyl (3S,4R)-3-methyl-1,6-diazaspiro[3.4]octane-1-carboxylate SR-MDOZ-OX: benzyl (3S,4R)-3-methyl-1,6-diazaspiro[3.4]octane-1-carboxylate oxalate SR-MDPZ: benzyl-(3S,4R)-3-methyl-6-(7H-pyrrolo[2,3-d]pyrimidin-4-yl)-1,6-diazaspiro[3.4]octane-1-carboxylate BHT: 2,6-di-tert-butyl-4-methylphenol DPCN: 1-cyanoacetyl-3,5-dimethyl-1H-pyrazole CPPY: 4-chloro-7H-pyrrolo[2,3-d]pyrimidine TBBA: bromoacetic acid tert-butyl ester PTFE: polytetrafluoroethylene The measuring instruments and measuring conditions used in the Examples are shown below.

$^1$H-NMR spectra are measured in CDCl$_3$, DMSO-d$_6$ or deuterium oxide using tetramethylsilane as an internal standard, and all δ values are reported as ppm. The measurement was performed by using NMR instrument at 400 MHz, unless otherwise specified.

Symbols in Examples have the meanings as shown below.
s: singlet
d: doublet
t: triplet
q: quartet
dd: double doublet
dq: double quartet
ddd: double double doublet
brs: broad singlet
m: multiplet
J: coupling constant The X-ray powder diffraction patterns of samples were measured by means of the powder X-ray diffractometry.
Measuring instrument: X'Pert Pro (SPECTRIS)
Measuring condition:
  Anticathode: Cu
  Tube current and voltage of X-ray tube bulb: 45 kV, 40 mA
  Rotary speed of sample: each 1 sec.
  Incident-beam Soller slit: 0.02 rad
  Incident-beam Vertical divergence slit: 15 mm
  Incident-beam Divergence slit: Auto, Irradiation width 15 mm
  Incident-beam Scattering slit: 1°
  Diffracted-beam Filter: Nickel filter
  Diffracted-beam Soller slit: 0.02 rad
  Diffracted-beam Divergence slit: Auto, Irradiation width 15 mm
  Detector: X'Celerator
  Detector mode: Scanning
  Effective width of Detector: 2.122°
  Scan axis: Gonio.
  Scan mode: Continuing
  Scan range: 3°-60°
  Time of unit step: 10 sec.

Each weight % of carbon, hydrogen and nitrogen in samples was determined by elemental analysis.

The average of measured values three times for a sample solution was an ion content in the sample.
Measuring instrument: Ion chromatograph LC-20 system (Shimadzu Corporation)
Measuring condition: Electrical-conductivity detector SHIMADZU CDD-10A VP
  Column for analysis of anions SHIMADZU SHIM-PAC IC-A3
  Column for analysis of cations SHIMADZU SHIM-PAC IC-C1

The content of water in a sample was determined by Karl Fischer titration.
Measuring instrument: Coulometric titrator for measurement of water contents CA-06 (Mitsubishi Chemical Corporation)
Measuring condition: Sample amount: about 20 mg
  Reagent: Anode solution Aquamicron AX (API Corporation)
  Cathode solution Aquamicron CXU (API Corporation)

Example 1

Preparation of a Co-Crystal (Compound [3-1]) of Compound A (Compound [4]) with 3,5-dimethylpyrazole (2:1, Molar Ratio) (Seed Crystal)

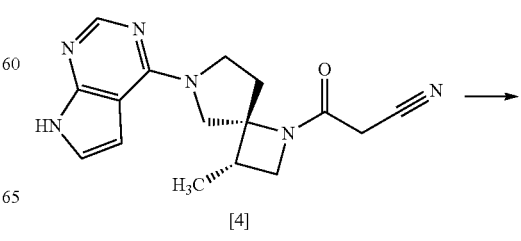

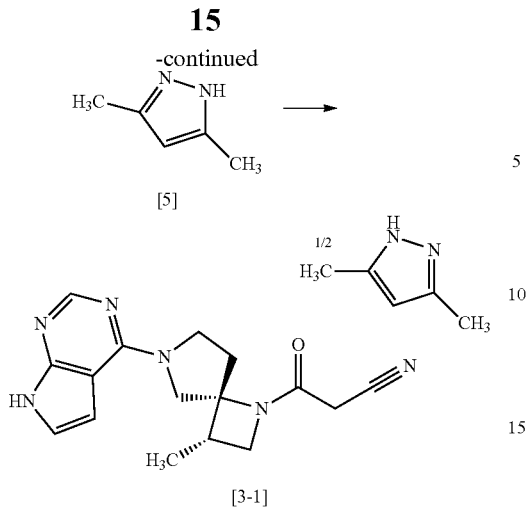

[5]

[3-1]

To Compound A (Compound [4]) (70.0 g, 226 mmol) and 3,5-dimethylpyrazole [5] (21.7 g, 226 mmol) was added acetonitrile (490 mL) under nitrogen atmosphere, and the mixture was dissolved with heating at 80° C. The mixture was stirred at 65° C. for 2 hrs. After precipitation of a crystal was observed, the mixture was gradually cooled to room temperature. After the mixture was stirred under ice cooling for 2 hrs, a precipitated solid was collected on a filter, and the obtained solid was washed with ice-cooled acetonitrile (140 mL). The obtained wet solid was dried under reduced pressure to give a co-crystal (Compound [3-1]) of Compound A (Compound [4]) with 3,5-dimethylpyrazole (2:1, molar ratio) (75.3 g, 210 mmol) in the yield of 93.1%.

NMR, elemental analysis, and differential scanning calorimetry were measured for the synthesized co-crystal of Compound A (Compound [4]) with 3,5-dimethylpyrazole (2:1, molar ratio).

$^1$H-NMR (DMSO-d$_6$) δ: 11.98 (br s, 0.5H), 11.59 (br s, 1H), 8.08 (s, 1H), 7.11 (dd, 1H, J=3.5, 2.2 Hz), 6.58 (dd, 1H, J=3.5, 1.4 Hz), 5.73 (s, 0.5H), 4.16 (t, 1H, J=8.3 Hz), 4.09-3.93 (m, 3H), 3.84-3.74 (m, 1H), 3.70 (d, 1H, J=19.0 Hz), 3.65 (d, 1H, J=19.0 Hz), 3.58 (dd, 1H, J=8.2, 5.9 Hz), 2.70-2.58 (m, 2H), 2.22-2.12 (m, 1H), 2.12 (s, 3H), 1.12 (d, 3H, J=7.2 Hz).

Elemental analysis: C, 61.9 wt %, H, 6.1 wt %, N, 27.2 wt % (Theoretical value C, 62.0 wt %, H, 6.2 wt %, N, 27.4 wt %)

Differential Scanning Calorimetry:

Measurement was conducted with a differential scanning calorimeter DSC-60A (manufactured by Shimadzu Corporation) at the rate of temperature increase of 5° C./min (sealed aluminum pan). A DSC curve obtained in the measurement is shown in FIG. 1. Enthalpy of endothermic peaks on the DSC curve was 100.26 J/g, the endothermic temperature was 173.66° C., and the extrapolated onset temperature was 172.36° C. The resulting spectrum is shown in FIG. 1.

The diffraction angle 2θ and the diffraction intensity were measured by powder X-ray diffractometry for the co-crystal of Compound A (Compound [4]) with 3,5-dimethylpyrazole (2:1, molar ratio). The resulting spectrum is shown in FIG. 2.

Figure 2:
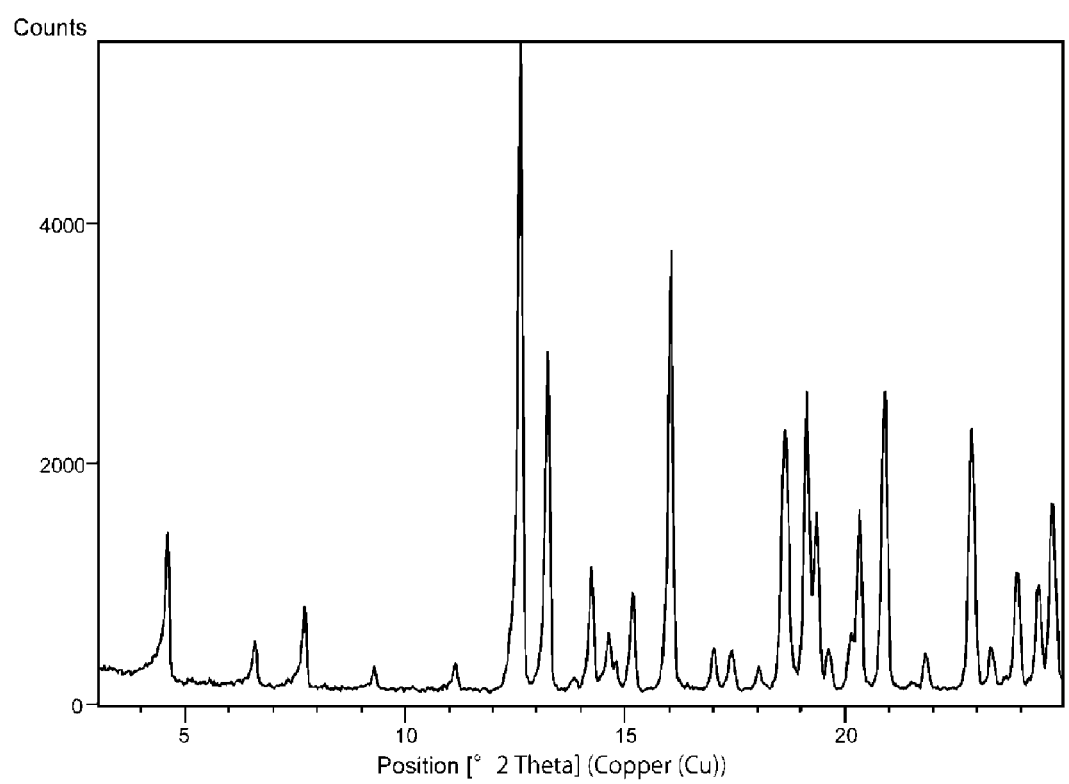
FIG. 2 shows a multiple record for powder X-ray diffraction pattern of a co-crystal (Compound [3-1]) of Compound A (Compound [4]) with 3,5-dimethylpyrazole (2:1, molar ratio) as a seed crystal. Diffraction intensity (cps: counts per second) is shown in the vertical axis, and diffraction angle 2θ (°) is shown in the horizontal axis.

The respective peaks in FIG. 2 are as shown in the following table.

| Diffraction angle [2θ (°)] | Relative intensity [%] | Diffraction intensity [cps] |
|---|---|---|
| 4.5995 | 22.59 | 1219.62 |
| 6.5864 | 6.80 | 367.17 |
| 7.7159 | 12.60 | 680.20 |
| 9.2996 | 3.43 | 185.09 |
| 11.1525 | 4.05 | 218.54 |
| 12.6288 | 100.00 | 5398.64 |
| 13.2491 | 52.15 | 2815.46 |
| 13.8436 | 1.87 | 101.04 |
| 14.2405 | 18.90 | 1020.43 |
| 14.6304 | 8.80 | 475.04 |
| 15.1842 | 15.26 | 823.69 |
| 16.0529 | 68.62 | 3704.73 |
| 17.0279 | 6.45 | 348.43 |
| 17.4374 | 6.06 | 327.35 |
| 18.0485 | 3.67 | 197.88 |
| 18.6535 | 39.95 | 2156.57 |
| 19.1303 | 45.91 | 2478.47 |
| 19.3693 | 26.84 | 1449.11 |
| 19.6389 | 6.22 | 335.68 |
| 20.3423 | 28.14 | 1519.44 |
| 20.9117 | 45.96 | 2481.20 |
| 21.8334 | 5.48 | 295.84 |
| 22.8850 | 40.22 | 2171.23 |
| 23.3477 | 6.21 | 335.04 |
| 23.9286 | 18.49 | 998.22 |
| 24.4043 | 16.04 | 866.13 |
| 24.7252 | 29.15 | 1573.95 |

Example 2

Preparation of a Co-Crystal (Compound [3-1]) of Compound A (Compound [4]) with 3,5-dimethylpyrazole (2:1, Molar Ratio)

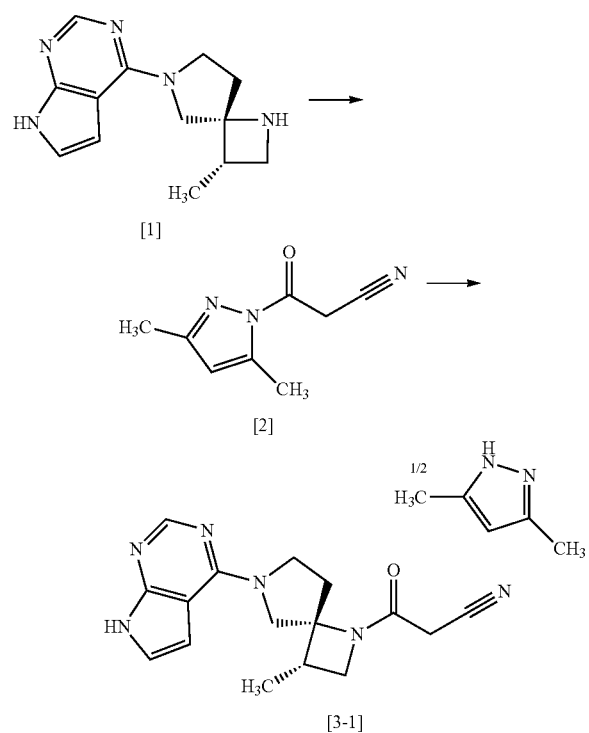

To SR-MDOP [1] (800 g, 3.29 mol) was added acetonitrile (8.0 L) under nitrogen atmosphere, and then to the mixture was added dropwise a solution of DPCN [2] (563 g, 3.45 mol) in acetonitrile (4.8 L) at 75° C. The dropping funnel used was washed with acetonitrile (0.8 L), and the washings were added to the reaction mixture. After the reaction mixture was stirred at 75° C. for 1.5 hrs, the reaction mixture was concentrated under reduced pressure to 8.0 L. To the residue was added at 65° C. the co-crystal (Compound [3-1]) of Compound A (Compound [4]) with 3,5-dimethylpyrazole (2:1, molar ratio) (80 mg) synthesized in Example 1. After stirring at 65° C. for 2 hrs, the mixture was stirred for 2 hrs under ice cooling. The precipitated solid was collected on a filter, and the resulting solid was washed with ice-cooled acetonitrile (2.4 L). The wet solid was dried under reduced pressure to give a co-crystal (Compound [3-1]) of Compound A (Compound [4]) with 3,5-dimethylpyrazole (2:1, molar ratio) (1070 g, 2.99 mol) in the yield of 90.8%.

NMR, elemental analysis, and differential scanning calorimetry were measured for the synthesized co-crystal of Compound A (Compound [4]) with 3,5-dimethylpyrazole (2:1, molar ratio).

$^1$H-NMR (DMSO-$d_6$) δ: 11.99 (br s, 0.5H), 11.59 (br s, 1H), 8.11 (s, 1H), 7.11 (s, 1H), 6.58 (d, 1H, J=3.0 Hz), 5.73 (s, 0.5H), 4.16 (t, 1H, J=8.4 Hz), 4.10-3.92 (m, 3H), 3.85-3.74 (m, 1H), 3.70 (d, 1H, J=19.1 Hz), 3.65 (d, 1H, J=19.1 Hz), 3.57 (dd, 1H, J=7.9, 6.1 Hz), 2.70-2.58 (m, 2H), 2.22-2.14 (m, 1H), 2.12 (s, 3H), 1.12 (d, 3H, J=6.9 Hz).

Elemental analysis: C, 62.0 wt %, H, 6.2 wt %, N, 27.2 wt % (Theoretical value C, 62.0 wt %, H, 6.2 wt %, N, 27.4 wt %)

Figure 3:
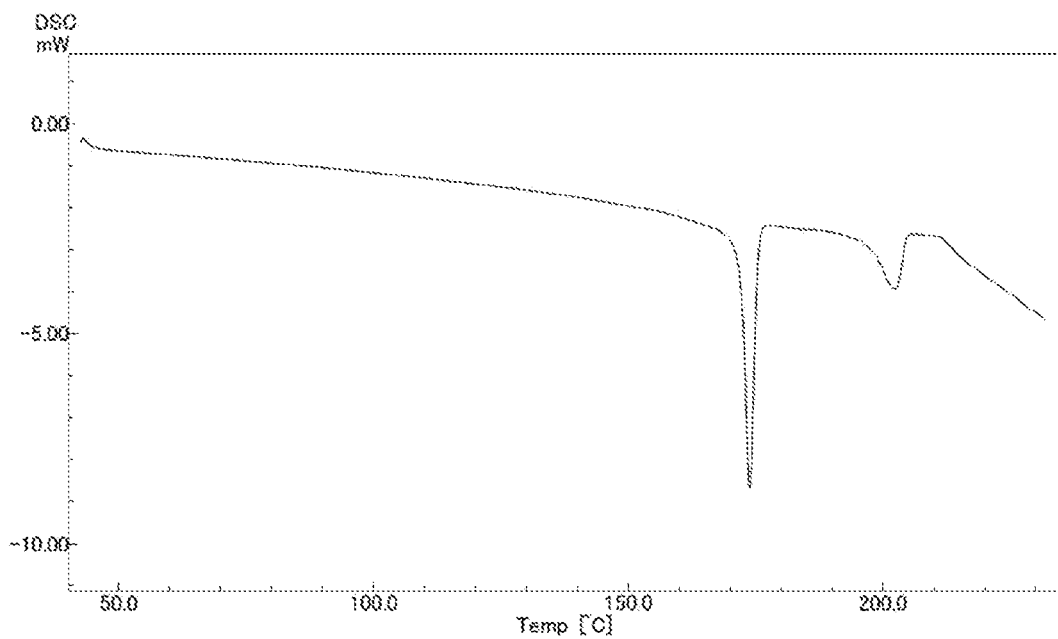
FIG. 3 shows a differential scanning calorimetry (DSC) curve for a co-crystal (Compound [3-1]) of Compound A (Compound [4]) with 3,5-dimethylpyrazole (2:1, molar ratio).

Differential Scanning Calorimetry:

Measurement was conducted with a differential scanning calorimeter DSC-60A (manufactured by Shimadzu Corporation) at the rate of temperature increase of 5° C./min (sealed aluminum pan). A DSC curve obtained in the measurement is shown in FIG. 3. Enthalpy of endothermic peaks on the DSC curve was 78.02 J/g, the endothermic temperature was 173.81° C., and the extrapolated onset temperature was 172.025° C. The resulting spectrum is shown in FIG. 3.

The diffraction angle 2θ and the diffraction intensity were measured by the powder X-ray diffractometry for the synthesized co-crystal of Compound A (Compound [4]) with 3,5-dimethylpyrazole (2:1, molar ratio). The resulting spectrum is shown in FIG. 4.

Figure 4:
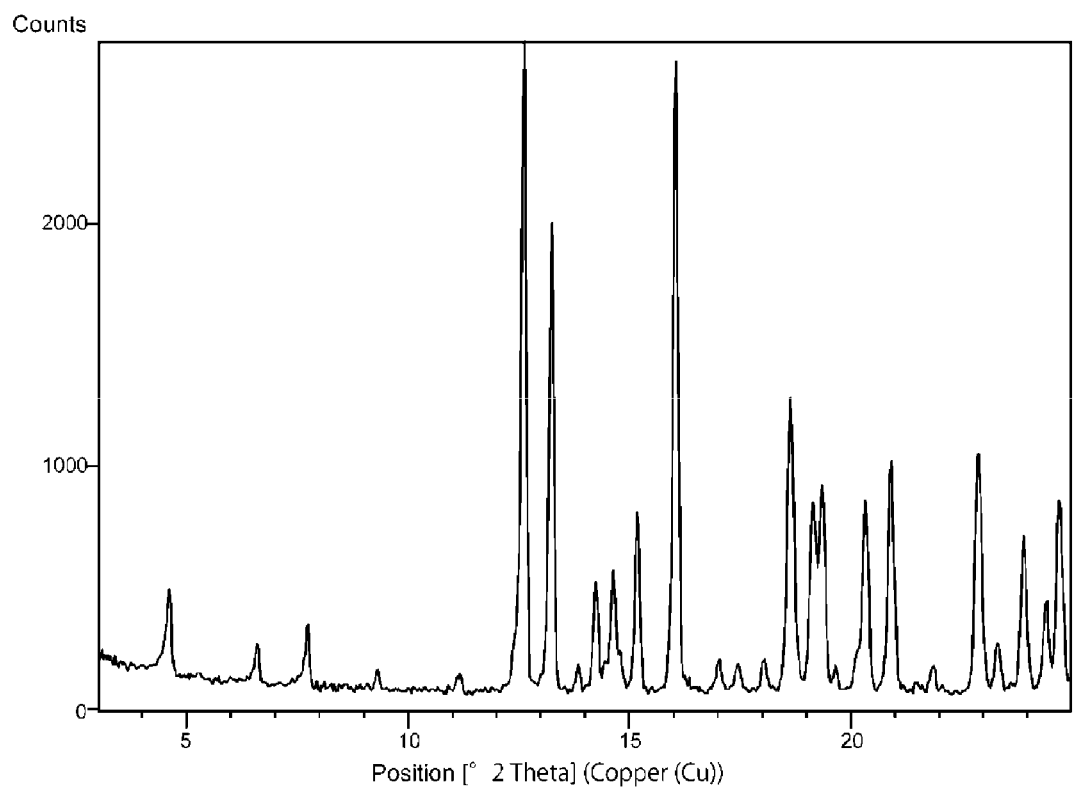
FIG. 4 shows a multiple record for powder X-ray diffraction pattern of a co-crystal (Compound [3-1]) of Compound A (Compound [4]) with 3,5-dimethylpyrazole (2:1, molar ratio). Diffraction intensity (cps: counts per second) is shown in the vertical axis, and diffraction angle 2θ (°) is shown in the horizontal axis.

The respective peaks in FIG. 4 are as shown in the following table.

| Diffraction angle [2θ (°)] | Relative intensity [%] | Diffraction intensity [cps] |
|---|---|---|
| 4.6074 | 12.69 | 341.47 |
| 6.5985 | 6.20 | 166.76 |
| 7.7215 | 9.57 | 257.49 |
| 9.3039 | 2.93 | 78.86 |
| 11.1582 | 2.08 | 56.00 |
| 12.6252 | 100.00 | 2690.94 |
| 13.2478 | 72.85 | 1960.46 |
| 13.8405 | 4.03 | 108.35 |
| 14.2414 | 16.75 | 450.87 |
| 14.6317 | 18.63 | 501.35 |
| 15.1837 | 27.93 | 751.46 |
| 16.0555 | 97.64 | 2627.45 |
| 17.0293 | 4.96 | 133.42 |
| 17.4558 | 4.29 | 115.36 |
| 18.0432 | 4.82 | 129.78 |
| 18.6385 | 45.15 | 1214.91 |
| 19.1352 | 29.44 | 792.08 |
| 19.3755 | 30.43 | 818.96 |
| 19.6628 | 4.02 | 108.11 |
| 20.3391 | 29.67 | 798.38 |
| 20.9048 | 35.47 | 954.60 |
| 21.8601 | 3.95 | 106.37 |
| 22.8816 | 36.84 | 991.38 |
| 23.3272 | 7.46 | 200.72 |
| 23.9114 | 23.73 | 638.46 |
| 24.4128 | 13.76 | 370.22 |
| 24.7091 | 29.29 | 788.13 |

Co-crystals wherein the molar ratios of Compound A (Compound [4]) and 3,5-dimethylpyrazole ranged from 2:0.842 to 2:0.864, in particular, 2:0.842, 2:0.848, 2:0.856, 2:0.862, and 2:0.864, were obtained in similar manners to Example 2.

Example 3

Preparation (Purification) of Compound A (Compound [4])

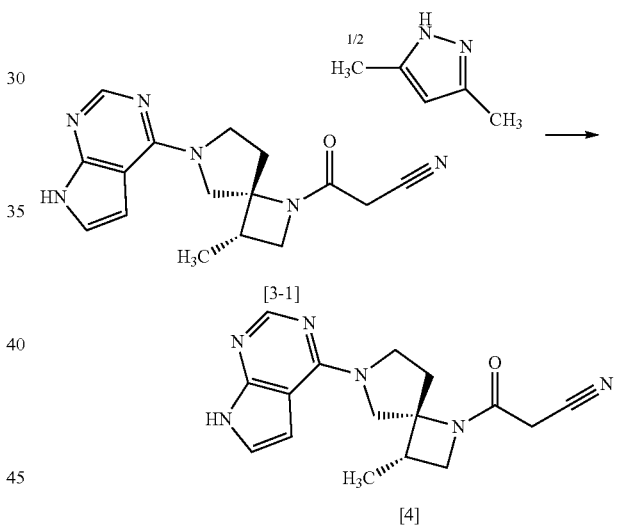

The co-crystal (Compound [3-1]) of Compound A (Compound [4]) with 3,5-dimethylpyrazole (2:1, molar ratio) (2.00 kg, 5.88 mol), BHT (60 g), and 1-butanol (16 L) were mixed under nitrogen atmosphere, and dissolved at 110° C. After the mixture was cooled to 85° C., the crystal (200 mg) of Compound A (Compound [4]) prepared preliminarily was added to the mixture. After stirring at 85° C. for 2 hrs, the mixture was gradually cooled to room temperature and stirred at room temperature for 3 hrs. The precipitated solid was collected on a filter, and the resulting solid was washed sequentially with 1-butanol (4 L) and ethyl acetate (4 L). The resulting wet solid was dried under reduced pressure to give Compound A (Compound [4]) (1.63 kg, 5.27 mol) in the yield of 94.4%.

NMR and MS were measured for Compound A (Compound [4]) that was synthesized in the same manner.

$^1$H-NMR (DMSO-$d_6$) δ: 11.58 (br s, 1H), 8.08 (s, 1H), 7.11 (dd, 1H, J=3.5, 2.3 Hz), 6.58 (dd, 1H, J=3.5, 1.6 Hz), 4.16 (t, 1H, J=8.4 Hz), 4.10-3.94 (m, 3H), 3.84-3.74 (m,

1H), 3.70 (d, 1H, J=19.0 Hz), 3.65 (d, 1H, J=18.7 Hz), 3.58 (dd, 1H, J=8.2, 5.9 Hz), 2.70-2.59 (m, 2H), 2.23-2.12 (m, 1H), 1.12 (d, 3H, J=7.2 Hz).

MS: m/z=311 [M+H]+

Example 4

Preparation of S-MABB-HC (Compound [6])

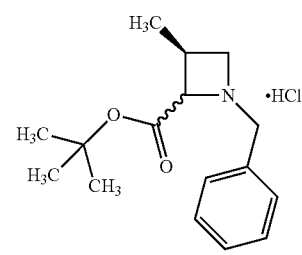

[6]

Step 1

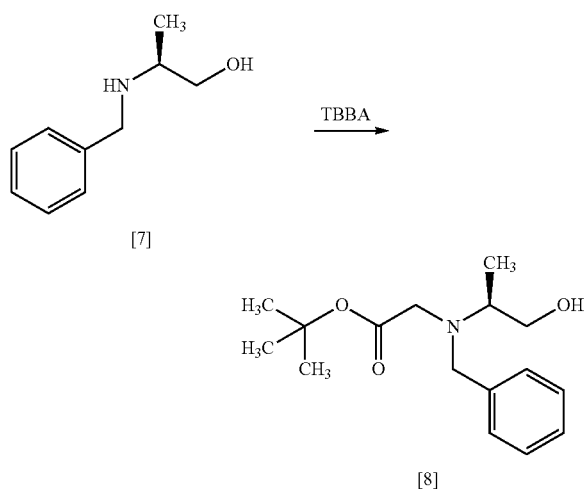

S-BAPO [7] (35.0 g, 212 mmol) was added to water (175 mL) at room temperature under nitrogen atmosphere. To the resulting suspension were added toluene (53 mL) and potassium carbonate (32.2 g, 233 mmol) at room temperature. To the resulting solution was added dropwise TBBA (434.4 g, 223 mmol) at room temperature, and then the used dropping funnel was washed with toluene (17 mL) and the washings were added to the reaction mixture. The reaction mixture was stirred at 65° C. for 21 hours, and then cooled to room temperature. After toluene (105 mL) was added to the reaction mixture and then the mixture was stirred, the organic layer was separated out. The organic layer was washed with water (175 mL), aqueous layer was removed, and then the solvent was removed out of the organic layer in vacuo. Toluene (105 mL) was added to the residue and the toluene solution was concentrated. The operation was repeated two more times to give a toluene solution of S-BBMO [8] (74.0 g, 212 mmol in theory). The given toluene solution of S-BBMO [8] was used in the next step, assuming that the yield was 100%.

A crude product of S-BBMO [8] that was synthesized in the same manner was concentrated and dried for measurement in NMR and MS.

¹H-NMR (DMSO-d$_6$) δ: 7.36-7.13 (5H, m), 4.26 (1H, dd, J 6.8, 3.9 Hz), 3.72 (2H, dd, J=14.2, 6.8 Hz), 3.47-3.38 (1H, m), 3.30-3.08 (3H, m), 2.79 (1H, sext, J=6.8 Hz), 1.35 (9H, s), 0.96 (3H, d, J=6.8 Hz).

MS: m/z=280 [M+H]$^+$

Step 2

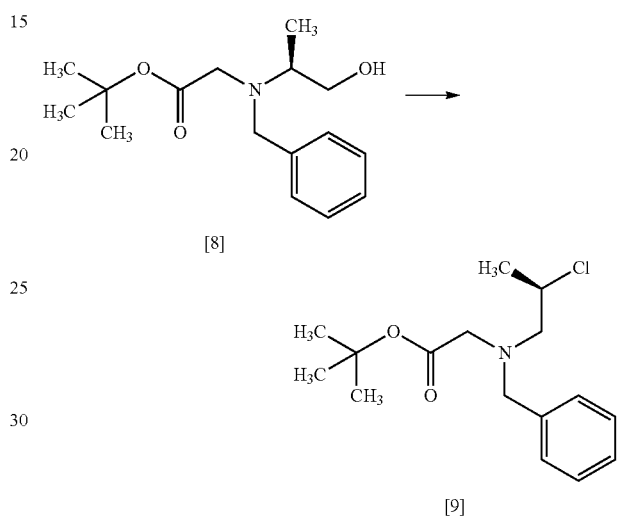

To the toluene solution of S-BBMO [8] (74.0 g, 212 mmol) were added toluene (200 mL), tetrahydrofuran (35 mL), and then triethylamine (25.7 g, 254 mmol) at room temperature under nitrogen atmosphere. To the mixture was added dropwise methanesulfonyl chloride (26.7 g, 233 mmol) at 0° C., and then the used dropping funnel was washed with toluene (10 mL) and the washings were added to the reaction mixture. The reaction mixture was stirred at room temperature for 2 hours and further at 65° C. for 22 hours, and then cooled to room temperature. After sodium bicarbonate water (105 mL) was added to the reaction mixture and then the mixture was stirred, the organic layer was separated out. The organic layer was washed with water (105 mL), aqueous layer was removed, and then the solvent was removed out of the organic layer in vacuo. Toluene (105 mL) was added to the residue, and the toluene solution was concentrated. The operation was repeated two more times to give a toluene solution of R-BCAB [9] (75.3 g, 212 mmol in theory). The given toluene solution of R-BCAB was used in the next step, assuming that the yield was 100%.

A crude product of R-BCAB that was synthesized in the same manner was concentrated and dried for measurement in NMR and MS.

¹H-NMR (DMSO-d$_6$) δ: 7.28-7.11 (5H, m), 4.24-4.11 (1H, m), 3.80 (2H, d, J=3.6 Hz), 3.24 (2H, d, J=3.6 Hz), 2.98-2.78 (2H, m), 1.46-1.37 (12H, m).

MS: m/z=298 [M+H]$^+$

Step 3

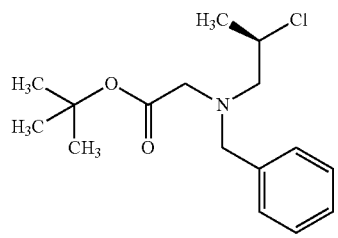

[9]

Step 4

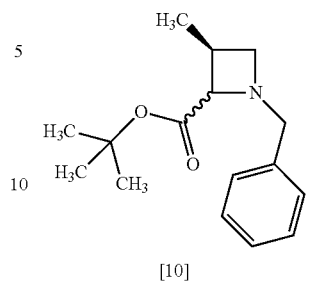

[10]

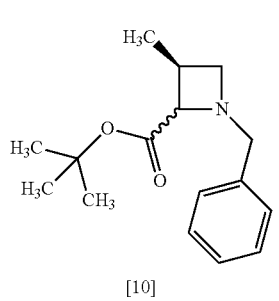

[10]

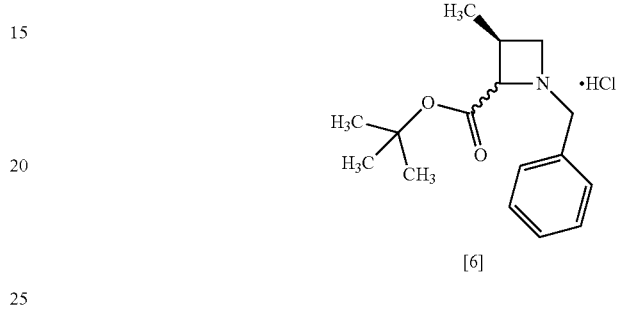

[6]

To the toluene solution of R-BCAB [9] (75.3 g, 212 mmol) were added tetrahydrofuran (88.0 mL) and 1,3-dimethyl-3,4,5,6-tetrahydro-2(1H)-pyrimidinone (42.0 mL) at room temperature under nitrogen atmosphere. To the resulting solution was added dropwise a solution of lithium bis(trimethylsilyl)amide/tetrahydrofuran (195 mL, 233 mmol) at 0° C., and then the used dropping funnel was washed with tetrahydrofuran (17.0 mL) and the washings were added to the reaction mixture. The reaction mixture was stirred at 0° C. for 1 hour, and then warmed to room temperature. After water (175 mL) and toluene (175 mL) were added to the reaction mixture and then the mixture was stirred, the organic layer was separated out. The resulting organic layer was washed with aqueous ammonium chloride (175 mL) and then water (175 mL), and the solvent was removed out of the organic layer in vacuo. Ethyl acetate (175 mL) was added to the residue and the ethyl acetate solution was concentrated. The operation was repeated two more times to give an ethyl acetate solution of S-MABB [10] (66.5 g, 212 mmol in theory). The given ethyl acetate solution of S-MABB was used in the next step, assuming that the yield was 100%.

A crude product of S-MABB [10] that was synthesized in the same manner was concentrated and dried for measurement in NMR and MS.

$^1$H-NMR (DMSO-$d_6$) δ: 7.28-7.25 (10H, m), 3.75 (1H, d, J=12.7 Hz), 3.68 (1H, d, J=1.4 Hz), 3.66 (1H, d, J=6.7 Hz), 3.46 (2H, d, J=12.7 Hz), 3.30-3.17 (2H, m), 2.95 (1H, dd, J=6.2, 1.2 Hz), 2.77 (1H, dd, J=6.1, 2.2 Hz), 2.65-2.55 (1H, m), 2.48-2.40 (2H, m), 1.35 (9H, s), 1.35 (9H, s), 1.12 (3H, d, J=7.2 Hz), 1.09 (3H, d, J=6.2 Hz).

MS: m/z=262 [M+H]$^+$

To the ethyl acetate solution of S-MABB [10] (66.5 g, 212 mmol in theory) were added ethyl acetate (175 mL) and active carbon (3.5 g) under nitrogen atmosphere, and then the mixture was stirred at room temperature for 2 hours. The active carbon was removed by filtration, and the residue on the filter was washed with ethyl acetate (175 mL). The washings were added to the filtrate. To the solution was added S-MABB-HC crystal (17.5 mg) that was prepared according to the method described herein at 0° C., and then 4 M hydrogen chloride/ethyl acetate (53.0 mL, 212 mmol) was dropped thereto at 0° C. The reaction mixture was stirred at 0° C. for 17 hours, and then the precipitated solid was collected on a filter, and washed with ethyl acetate (70 mL). The resulting wet solid was dried in vacuo to give S-MABB-HC [6] (48.3 g, 162 mmol, yield: 76.4%).

NMR, MS, and Cl-content were measured for S-MABB-HC [6] that was synthesized in the same manner.

$^1$H-NMR (DMSO-$d_6$) δ: 11.08 (1H, br s), 10.94 (1H, br s), 7.52-7.42 (10H, m), 5.34 (1H, t, J=8.4 Hz), 4.90 (1H, br s), 4.45-4.10 (5H, m), 3.92-3.49 (3H, br m), 3.10-2.73 (2H, br m), 1.35 (9H, s), 1.29 (9H, s), 1.24 (3H, d, J=6.7 Hz), 1.17 (3H, d, J=7.4 Hz).

MS: m/z=262 [M+H-HCl]$^+$

Cl content (ion chromatography): 11.9% (11.9% in theory)

Example 5

Preparation of S-MACB-HC (Compound [11])

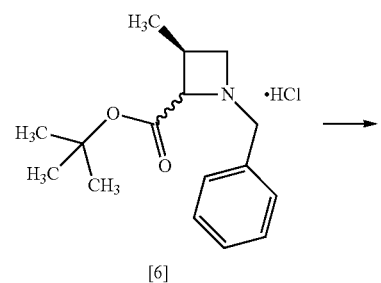

[6]

-continued

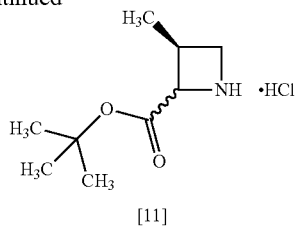

[11]

To a solution of S-MABB-HC [6] (5.0 g, 16.8 mmol) in methanol (15.0 mL) was added 5% palladium carbon (made by Kawaken Fine Chemicals Co., Ltd., PH type, 54.1% water-content 1.0 g) at room temperature under nitrogen atmosphere. The reaction vessel was filled with hydrogen, the reaction mixture was stirred at hydrogen pressure of 0.4 MPa at room temperature for 12 hours, the hydrogen in the reaction vessel was replaced with nitrogen, and then the 5% palladium carbon was removed by filtration. The reaction vessel and the 5% palladium carbon were washed with methanol (10 mL). The washings were added to the filtrate to give a methanol solution of S-MACB-HC [11] (24.8 g, 16.8 mmol in theory). The given methanol solution of S-MACB-HC was used in the next step, assuming that the yield was 100%.

A crude product of S-MACB-HC that was synthesized in the same manner was concentrated and dried for measurement in NMR and MS.

$^1$H-NMR (DMSO-d$_6$) δ: 9.60 (br s, 1H), 4.97 (d, 1H, J=9.2 Hz), 4.61 (d, 1H, J=8.4 Hz), 4.01 (dd, 1H, J=10.0, 8.4 Hz), 3.78-3.74 (m, 1H), 3.54 (dd, 1H, J=9.6, 8.4 Hz), 3.35 (dd, 1H, J=10.0, 6.0 Hz), 3.15-3.03 (m, 1H), 3.00-2.88 (m, 1H), 1.49 (s, 9H), 1.47 (s, 9H), 1.22 (d, 3H, J=6.8 Hz), 1.14 (d, 3H, J=7.2 Hz).

MS: m/z=172 [M+H]$^+$ (free form)

Example 6

Preparation of S-ZMAB (Compound [12])

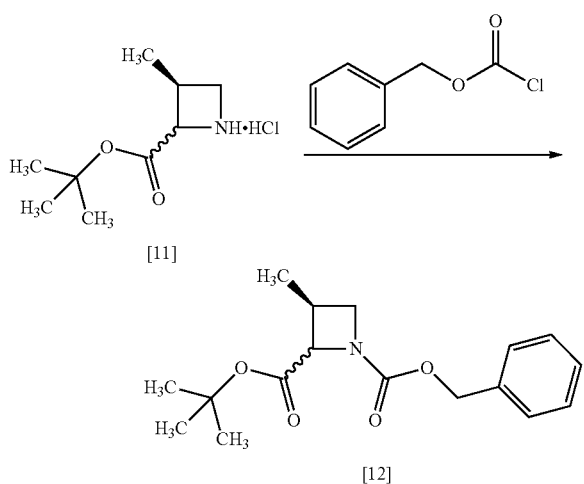

To the methanol solution of S-MACB-HC [11] (24.8 g, 16.8 mmol in theory) was added dropwise N,N-diisopropylethylamine (4.8 g, 36.9 mmol) at room temperature under nitrogen atmosphere, and then the used dropping funnel was washed with tetrahydrofuran (2.5 mL) and the washings were added to the reaction mixture. To the resulting reaction mixture was added dropwise benzyl chloroformate (3.0 g, 17.6 mmol) at 0° C., and then the used dropping funnel was washed with tetrahydrofuran (2.5 mL) and the washings were added to the reaction mixture. The reaction mixture was stirred at 0° C. for 1 hour, and then the solvent was removed in vacuo. After toluene (25.0 mL) and an aqueous solution of citric acid (25.0 mL) was added to the residue and then the mixture was stirred, the organic layer was separated out. The resulting organic layer was washed with sodium bicarbonate water (25.0 mL) and then water (25.0 mL), and the solvent in the organic layer was removed out of the organic layer in vacuo. Toluene (15.0 mL) was added to the residue and the toluene solution was concentrated. The operation was repeated one more time to give a toluene solution of S-ZMAB [12] (6.9 g, 16.8 mmol in theory). The given toluene solution of S-ZMAB was used in the next step, assuming that the yield was 100%.

A crude product of S-ZMAB that was synthesized in the same manner was concentrated and dried for measurement in NMR and MS.

$^1$H-NMR (CDCl$_3$) δ: 7.38-7.28 (m, 10H), 5.16-5.04 (m, 4H), 4.60 (d, 1H, J=9.2 Hz), 4.18-4.12 (m, 2H), 4.04 (t, 1H, J=8.6 Hz), 3.66 (dd, 1H, J=7.6, 7.2 Hz), 3.50 (dd, 1H, J=8.0, 5.2 Hz), 3.05-2.94 (m, 1H), 2.60-2.50 (m, 1H), 1.43 (br s, 18H), 1.33 (d, 3H, J=6.5 Hz), 1.15 (d, 3H, J=7.2 Hz).

MS: m/z=328 [M+Na]$^+$

Example 7

Preparation of RS-ZMBB (Compound [13])

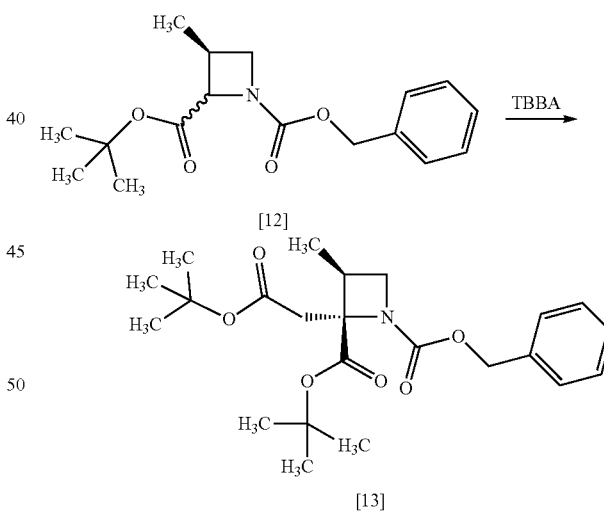

To the toluene solution of S-ZMAB [12] (6.9 g, 16.8 mmol) was added tetrahydrofuran (15.0 mL) at room temperature under nitrogen atmosphere. A solution of lithium bis(trimethylsilyl)amide/tetrahydrofuran (14.7 mL, 17.6 mmol) was added dropwise to the toluene solution at −70° C. The used dropping funnel was washed with tetrahydrofuran (2.5 mL) and the washings were added to the reaction mixture. The reaction mixture was stirred at −70° C. for 6 hours, and then a solution of TBBA (3.4 g, 17.6 mmol) in tetrahydrofuran (2.5 mL) was added dropwise to the reaction mixture at −70° C. The used dropping funnel was washed with tetrahydrofuran (2.5 mL) and the washings were added to the reaction mixture. The reaction mixture was stirred at −70° C. for 1 hour, and then warmed to room temperature. To the reaction mixture were added an aqueous ammonium chloride (25 mL) and toluene (25 mL) and then the mixture was stirred, the organic layer was separated out. The resulting organic layer was washed with an aqueous solution of citric acid (25 mL×2), sodium bicarbonate water (25 mL), and then water (25 mL), and then the solvent was removed out of the organic layer in vacuo. Acetonitrile (15 mL) was added to the residue and the acetonitrile solution was concentrated. The operation was repeated two more times. Acetonitrile (15 mL) and active carbon (0.25 g) were added to the residue, the mixture was stirred at room temperature for 2 hours. The active carbon was removed by filtration, and the reaction vessel and the residue on the filter was washed with acetonitrile (10 mL). The washings were added to the filtration, and then the filtration was concentrated in vacuo to give an acetonitrile solution of RS-ZMBB [13] (13.2 g, 16.8 mmol in theory). The given acetonitrile solution of RS-ZMBB was used in the next step, assuming that the yield was 100%.

A crude product of RS-ZMBB that was synthesized in the same manner was concentrated and dried for measurement in NMR and MS.

$^1$H-NMR (DMSO-$d_6$) δ: 7.38-7.29 (m, 5H), 5.09-4.96 (m, 2H), 3.91 (t, 0.4H, J=8.0 Hz), 3.79 (t, 0.6H, J=8.0 Hz), 3.55 (t, 0.4H, J=7.2 Hz), 3.46 (t, 0.6H, J=7.5 Hz), 3.14-3.04 (m, 1H), 2.83-2.72 (m, 2H), 1.38 (br s, 9H), 1.37 (br s, 3.6H), 1.34 (br s, 5.4H), 1.12-1.09 (m, 3H).

MS: m/z=420 [M+H]$^+$

Example 8

Preparation of RS-ZMAA-DN.2H$_2$O (Compound [14])

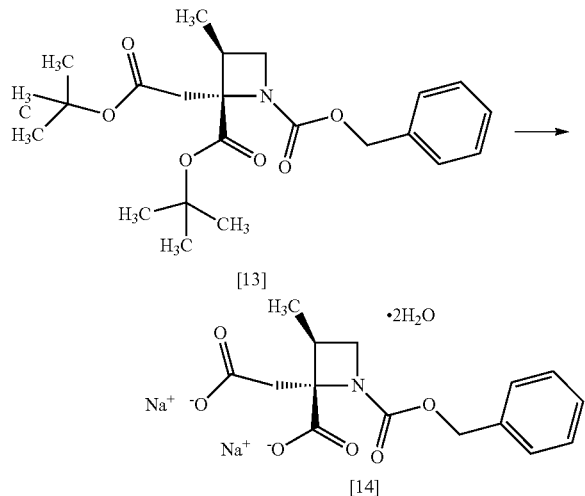

To the acetonitrile solution of RS-ZMBB [13] (13.2 g, 16.8 mmol in theory) was added acetonitrile (15 mL) at room temperature under nitrogen atmosphere. p-Toluenesulfonic acid mono-hydrate (6.4 g, 33.6 mmol) was added to the solution at room temperature. The reaction mixture was stirred at 50° C. for 12 hours, and then cooled to room temperature, and water (7.5 mL) was added dropwise to the reaction mixture. The reaction mixture was cooled to 0° C., and then 4 mol/L aqueous sodium hydroxide (17.6 mL, 70.5 mmol) was added dropwise thereto. After stirring the reaction mixture at room temperature for 1 hour, acetonitrile (75 mL) was added dropwise thereto at room temperature, and the reaction mixture was stirred for 3 hours. The precipitated solid was collected on a filter, and washed with a mixture of acetonitrile:water=4:1 (10 mL) and then acetonitrile (10 mL). The resulting wet solid was dried in vacuo to give RS-ZMAA-DN.2H$_2$O [14] (5.2 g, 13.4 mmol, yield: 85.4%).

NMR, MS, Na-content, and water-content were measured for RS-ZMAA-DN.2H$_2$O that was prepared in the same manner.

$^1$H-NMR (DMSO-$d_6$) δ: 7.32-7.22 (m, 5H), 4.97 (d, 1H, J 12.7 Hz), 4.84 (d, 1H, J=12.7 Hz), 3.79 (t, 1H, J=8.0 Hz), 3.29 (d, 1H, J=14.8 Hz), 3.16-3.12 (m, 1H), 2.17-2.09 (m, 2H), 1.07 (d, 3H, J=6.9 Hz).

MS: m/z=352 [M+H]$^+$ (anhydrate)

Na content (ion chromatography): 13.3% (after correction of water content) (13.1% in theory)

Water content (Karl Fischer's method): 9.8% (9.3% in theory)

Example 9

Preparation of RS-ZMAA (Compound [15])

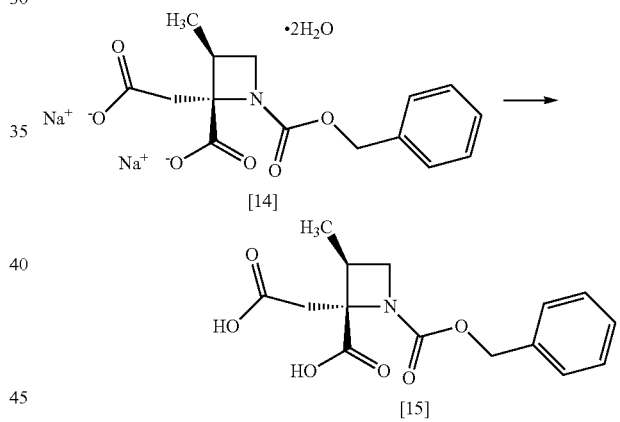

To 1 mol/L hydrochloric acid (180 mL) were added RS-ZMAA-DN.2H$_2$O [14] (30 g, 77.5 mmol) and acetonitrile (60 mL), and the mixture was stirred at room temperature for about 15 minutes. After ethyl acetate (240 mL) was added to the reaction mixture and then the mixture was stirred, the organic layer was separated out. The organic layer was washed with 10% brine (60 mL×2). The organic layer was stirred with magnesium sulfate (6 g), the magnesium sulfate was removed by filtration, and the residue on the filter was washed with ethyl acetate (60 mL). The filtrate and the washings are combined, and the solvent was removed out in vacuo. Tetrahydrofuran (240 mL) was added to the residue and the tetrahydrofuran solution was concentrated. The operation was repeated two more times. Tetrahydrofuran (60 mL) was added to the residue to give a tetrahydrofuran solution of RS-ZMAA [15]. The given tetrahydrofuran solution of RS-ZMAA was used in the next step, assuming that the yield was 100%.

NMR and MS were measured for RS-ZMAA that was prepared in the same manner.

¹H-NMR (DMSO-D₆) δ: 7.35-7.28 (m, 5H), 5.06-4.94 (m, 2H), 3.86 (dt, 1H, J=48.4, 7.9 Hz), 3.50 (dt, 1H, J=37.9, 7.4 Hz), 3.16-3.02 (br m, 1H), 2.91-2.77 (br m, 2H), 1.08 (d, 3H, J=6.9 Hz)

MS: m/z=308 [M+H]⁺

Example 10

Preparation of RS-ZMOO (Compound [16])

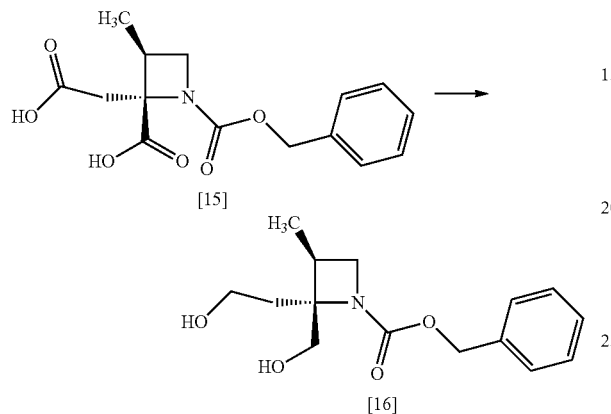

To the tetrahydrofuran solution of RS-ZMAA [15] (25.8 mmol in theory) was added tetrahydrofuran (50 mL) under nitrogen atmosphere. Boron trifluoride etherate complex (4.40 g) was added dropwise thereto at 0° C. to 5° C. The used dropping funnel was washed with tetrahydrofuran (5 mL) and the washings were added to the reaction mixture. To the reaction mixture was added dropwise 1.2 mol/L borane-tetrahydrofuran complex (43.0 mL) at 0° C. to 5° C., and the reaction mixture was stirred at 0° C. to 5° C. for about 30 minutes, and then further stirred at room temperature overnight. To the reaction mixture was added dropwise 1.2 mol/L borane-tetrahydrofuran complex (21.1 mL) at 0° C. to 5° C., and then the reaction mixture was stirred at room temperature overnight. After stirring, water (40 mL) was added dropwise to the reaction mixture at 0° C. to 15° C. To the reaction mixture was added sodium bicarbonate (5.42 g) at 0° C. to 15° C. The sodium bicarbonate left in the vessel was washed with water (10 mL), and the washings were added to the reaction mixture. The reaction mixture was stirred at room temperature for 2 hours, and then toluene (50 mL) was added thereto and the reaction mixture was further stirred. The organic layer was separated out. The resulting organic layer was washed with 10% brine (20 mL×1), a mixture (×3) of 5% sodium bicarbonate water (20 mL) and 10% brine (20 mL), a mixture (×1) of 5% aqueous potassium hydrogensulfate (10 mL) and 10% brine (10 mL), and then 10% brine (20 mL×2). The organic layer was stirred with magnesium sulfate (8.9 g), the magnesium sulfate was removed by filtration, and the residue on the filter was washed with toluene (20 mL). The washings were added to the filtration, and then the filtrate was concentrated in vacuo. To the concentrated residue was added toluene (80 mL). The solution was concentrated in vacuo, and toluene (15 mL) was added thereto to give a toluene solution of RS-ZMOO [16]. The given toluene solution of RS-ZMOO was used in the next step, assuming that the yield was 100%.

NMR and MS were measured for RS-ZMOO that was prepared in the same manner.

¹H-NMR (CDCl₃) δ: 7.39-7.30 (m, 5H), 5.10 (s, 2H), 4.15-4.01 (br m, 2H), 3.83-3.73 (br m, 3H), 3.48 (dd, 1H, J=8.3, 6.4 Hz), 2.59-2.50 (br m, 1H), 2.46-2.40 (br m, 1H), 2.07-1.99 (m, 1H), 1.14 (d, 3H, J=7.2 Hz)

MS: m/z=280 [M+H]⁺

Example 11

Preparation of RS-ZMSS (Compound [17])

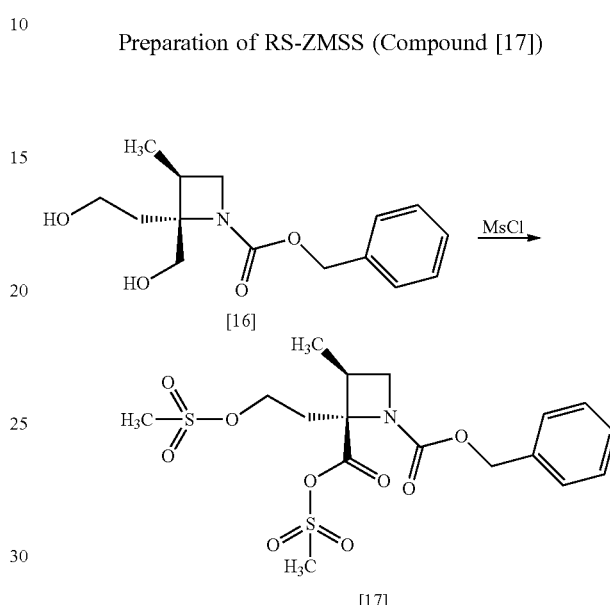

To the toluene solution of RS-ZMOO [16] (23.7 mmol in theory) was added toluene (55 mL) under nitrogen atmosphere. And, triethylamine (5.27 g) was added dropwise thereto at −10° C. to 10° C., and the used dropping funnel was washed with toluene (1.8 mL) and the washings were added to the reaction mixture. To this reaction mixture was added dropwise methanesulfonyl chloride (5.69 g) at −10° C. to 10° C., and then the used dropping funnel was washed with toluene (1.8 mL) and the washings were added to the reaction mixture. The reaction mixture was stirred at 0° C. to 10° C. for about 2 hours, and then water (28 mL) was added dropwise thereto at 0° C. to 20° C. The reaction mixture was stirred at 0° C. to 20° C. for about 30 minutes, and then, the organic layer was separated out. The resulting organic layer was washed twice with 10% brine (18 mL). The organic layer was stirred with magnesium sulfate (2.75 g), the magnesium sulfate was removed by filtration, and the residue on the filter was washed with toluene (18 mL). The washings were added to the filtrate, and then the solvent was removed from the filtrate in vacuo. To the concentrated residue was added toluene up to 18 mL to give a toluene solution of RS-ZMSS [17]. The given toluene solution of RS-ZMSS was used in the next step, assuming that the yield was 100%.

NMR and MS were measured for RS-ZMSS that was prepared in the same manner.

¹H-NMR (DMSO-D₆) δ: 7.37-7.27 (br m, 5H), 5.10-4.98 (m, 2H), 4.58-4.22 (br m, 4H), 3.84 (dt, 1H, J=45.6, 8.1 Hz), 3.48-3.33 (br m, 1H), 3.17-3.10 (m, 6H), 2.81-2.74 (br m, 1H), 2.22-2.12 (m, 2H)

MS: m/z=436 [M+H]⁺

Example 12

Preparation of SR-ZMDB (Compound [18])

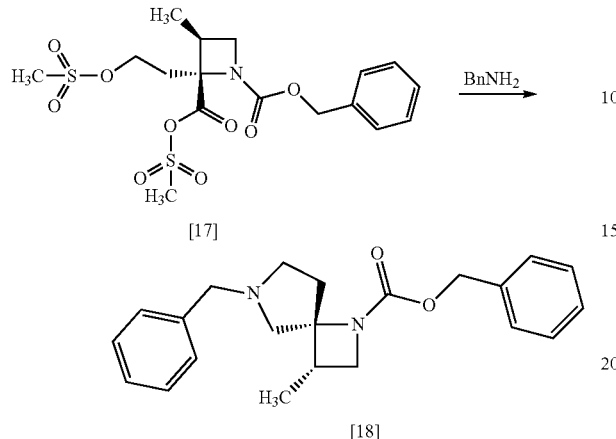

Example 13

Preparation of SR-MDOZ (Compound [19])

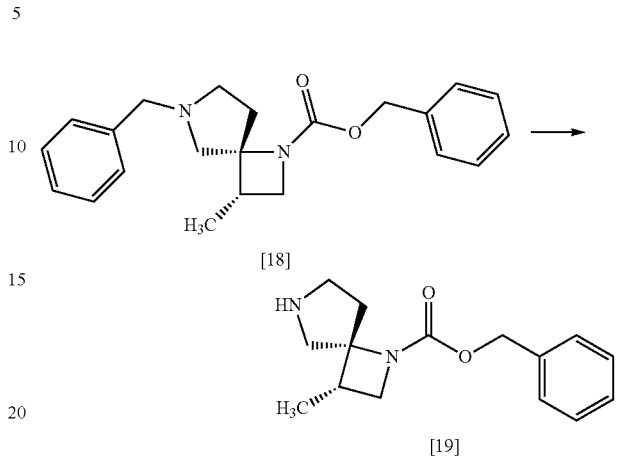

To a toluene solution of RS-ZMSS [17] (23.7 mmol in theory) was added toluene (55 mL) under nitrogen atmosphere. And, benzylamine (17.8 g) was added dropwise thereto at room temperature, and the used dropping funnel was washed with toluene (9.2 mL) and the washings were added to the reaction mixture. The reaction mixture was stirred at room temperature for about 1 hour, at 55° C. to 65° C. for about 3 hours, and then at 70° C. to 80° C. for 6 hours. After the reaction mixture was cooled to room temperature, 10% NaCl (28 mL) was added dropwise thereto, and the reaction mixture was stirred at room temperature for about 30 minutes. After toluene (37 mL) was added to the reaction mixture and then the mixture was stirred, the organic layer was separated out. The resulting organic layer was washed with a mixture (×2) of 10% brine (18 mL) and acetic acid (2.84 g), and then 10% brine (11 mL×1). The solvent of the organic layer was removed in vacuo to a half volume, and acetic anhydride (1.45 g) was added to the concentrated residue at room temperature. The mixture was stirred for about 3 hours. To the reaction mixture were added dropwise a solution of potassium hydrogensulfate (3.87 g) and water (92 mL) at room temperature. The reaction mixture was stirred, and then the aqueous layer was separated out. The resulting aqueous layer was washed with toluene (18 mL), and toluene (73 mL) and then sodium bicarbonate (6.56 g) were added to the aqueous layer at room temperature, and the mixture was stirred. The organic layer was separated out, and washed with 10% brine (11 mL). The organic layer was stirred with magnesium sulfate (2.75 g), and the magnesium sulfate was removed by filtration. The residue on the filter was washed with toluene (18 mL), and the washings were added to the filtrate, and then the filtrate was concentrated in vacuo. Toluene (44 mL) was added to the concentrated residue to give a toluene solution of SR-ZMDB [18]. The given toluene solution of SR-ZMDB was used in the next step, assuming that the yield was 100%.

$^1$H-NMR (CDCl$_3$) δ: 7.35-7.20 (m, 10H), 5.08 (d, 2H, J=23.6 Hz), 3.94 (q, 1H, J=7.9 Hz), 3.73-3.42 (br m, 2H), 3.30-3.23 (m, 1H), 3.05 (dd, 1H, J=19.7, 9.5 Hz), 2.79 (dt, 1H, J=69.6, 6.1 Hz), 2.57-2.32 (br m, 4H), 1.96-1.89 (m, 1H), 1.09 (d, 3H, J=6.9 Hz)

MS: m/z=351 [M+H]$^+$

To a solution of 1-chloroethyl chloroformate (3.72 g) and toluene (28 mL) was added dropwise a solution of SR-ZMDB [18] in toluene (corresponding to 23.7 mmol) under nitrogen atmosphere in the range between 0° C. and 10° C. The dropping funnel was washed with toluene (4.6 mL), and the washings were added to the reaction mixture. To the reaction mixture was added triethylamine (718 mg) in the range between 0° C. and 10° C., and the mixture was stirred in the range between 15° C. and 25° C. for about 2 hr. Then, thereto was added methyl alcohol (46 mL), and the mixture was stirred in the range between 50° C. and 60° C. for additional about 2 hr. The solvent of the reaction mixture was removed under reduced pressure so that the residue was in about 37 mL or less. To the concentrated residue was added dropwise 2 mol/L hydrochloric acid solution (46 mL) in the range between 15° C. and 20° C., and the mixture was stirred. Then, the aqueous layer was separated. The resulting aqueous layer was washed with toluene (28 mL) twice. To the aqueous layer were added 20% brine (46 mL) and tetrahydrofuran (92 mL), and then thereto was added dropwise 8 mol/L aqueous sodium hydroxide solution (18 mL) in the range between 0° C. and 10° C. The organic layer was separated from the reaction mixture, and the resulting organic layer was washed with 20% brine (18 mL) twice, and then the solvent of the organic layer was removed under reduced pressure. The procedure where tetrahydrofuran (92 mL) was added to the concentrated residue and the mixture was concentrated under reduced pressure was performed twice. The concentrated residue was dissolved in tetrahydrofuran (92 mL), and thereto was added magnesium sulfate (2.75 g). The mixture was stirred and magnesium sulfate was filtered off. The filtered residue was washed with tetrahydrofuran (28 mL), and the filtrate and the washings were collected and the solvent was removed under reduced pressure. The amount of the concentrated residue was adjusted with tetrahydrofuran to be about 20 mL to give a solution of SR-MDOZ [19] in tetrahydrofuran (net amount: 4.01 g, 15.4 mol) in the yield of 65.0%.

SR-MDOZ that was synthesized in the same manner was concentrated and dried for measurement in NMR and MS.

$^1$H-NMR (CDCl$_3$) δ: 7.37-7.28 (m, 5H), 5.08 (dd, 2H, J=16.8, 12.8 Hz), 4.00 (dd, 1H, J=17.1, 8.3 Hz), 3.40-3.31

(m, 1H), 3.24 (d, 1H, J=12.7 Hz), 3.00 (dd, 1H, J=54.9, 12.4 Hz), 2.87-2.57 (m, 3H), 2.47-2.27 (m, 1H), 1.91-1.80 (m, 1H), 1.14 (d, 3H, J=7.2 Hz)

MS: m/z=261 [M+H]+

Example 14

Preparation of SR-MDOZ-OX (Compound [20])

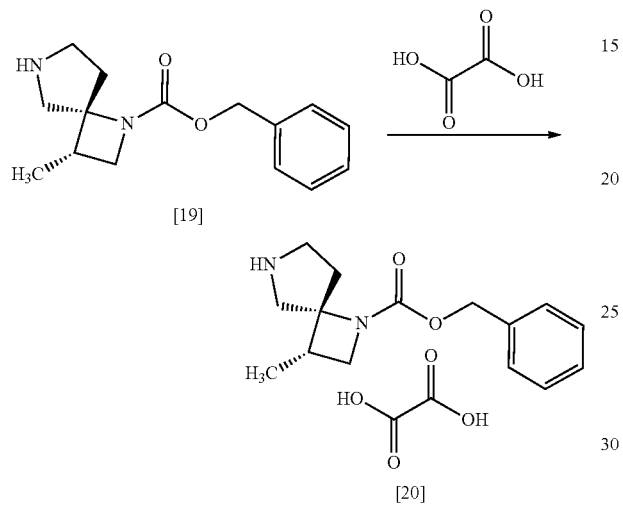

Oxalic acid (761 mg) was dissolved in tetrahydrofuran (40 mL) under nitrogen atmosphere, and then thereto was added dropwise a solution of SR-MDOZ [19] in tetrahydrofuran (corresponding to 3.84 mmol) at room temperature. To this solution was added at room temperature a crystal of SR-MDOZ-OX (1 mg) that was prepared in advance in the same manner to the present procedure. The mixture was stirred at room temperature for about 3.5 hours to precipitate a crystal. To this slurry was added dropwise a solution of SR-MDOZ in tetrahydrofuran (3.84 mmol) at room temperature, and the mixture was stirred at room temperature for about 1 hour. This slurry was heated and stirred at 50° C. to 60° C. for about 2 hours, and then stirred at room temperature overnight. This slurry was filtered, and a wet crystal was washed with tetrahydrofuran (10 mL) and dried under reduced pressure to give SR-MDOZ-OX [20] (2.32 g, 6.62 mol) in the yield of 86.2%.

NMR, MS, and elemental analysis were measured for SR-MDOZ-OX that was synthesized in the same manner.

$^1$H-NMR (DMSO-D$_6$) δ: 7.37-7.30 (m, 5H), 5.15-5.01 (m, 2H), 3.92 (dt, 1H, J=43.5, 8.4 Hz), 3.48-3.12 (br m, 5H), 2.67-2.56 (m, 1H), 2.46-2.35 (m, 1H), 2.12-2.05 (m, 1H), 1.13 (d, 3H, J=6.9 Hz)

MS: m/z=261 [M+H]+

Elemental analysis: C, 58.4 wt %, H, 6.4 wt %, N, 7.9 wt %

(Theoretical value C, 58.3 wt %, H, 6.3 wt %, N, 8.0 wt %)

Example 15

Preparation of SR-MDPZ (Compound [21])

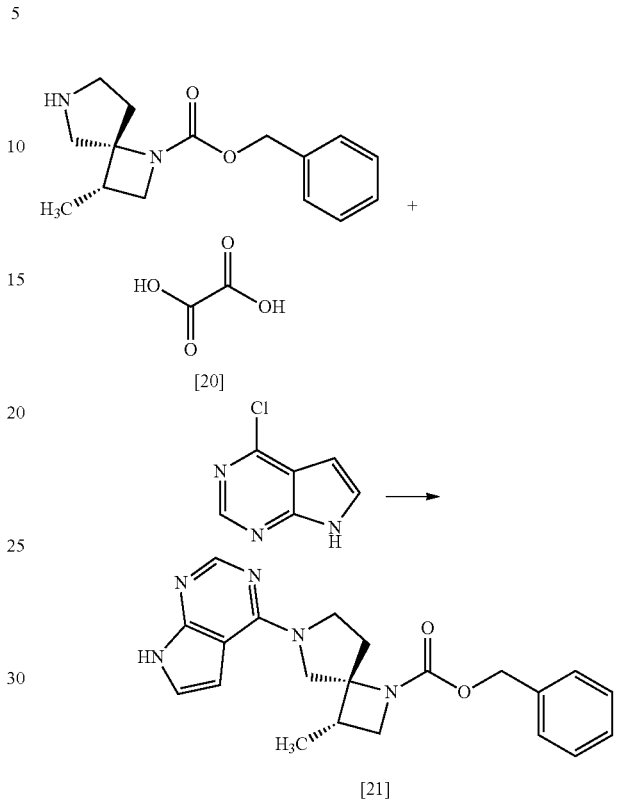

To SR-MDOZ-OX [20] (12.0 g, 34.2 mmol) was added ethanol (36 mL) under nitrogen atmosphere, and then thereto were added sequentially water (72 mL), CPPY (5.36 g, 34.9 mmol), and K$_3$PO$_4$ (21.8 g, 103 mmol). The reaction mixture was stirred at 80° C. for 5 hours, and then cooled to 40° C. Then, thereto was added toluene (120 mL) at 40° C., and the organic layer was separated. The resulting organic layer was washed with 20% aqueous potassium carbonate solution (48 mL), and then washed with water (48 mL) twice. Then, the solvent of the organic layer was removed under reduced pressure. tert-Butanol (60 mL) was added to this concentrated residue. The concentration operation was repeated three times. To the concentrated residue was added tert-butanol (36 mL), and a solution of SR-MDPZ [21] in tert-butanol (61.1 g, corresponding to 34.2 mmol) was afforded. The resulting solution of SR-MDPZ in tert-butanol was used in the next step, assuming that the yield was 100%.

SR-MDPZ that was synthesized in the same manner was obtained as a solid with treatment of a mixed solvent of ethyl acetate and n-heptane, for which NMR and MS were measured.

$^1$H-NMR (DMSO-d$_6$) δ: 11.59 (br s, 1H), 8.08 (s, 1H), 7.41-7.26 (br m, 3H), 7.22-7.08 (br m, 3H), 6.64-6.51 (br m, 1H), 5.07-4.91 (br m, 2H), 4.09-3.67 (br m, 5H), 3.47-3.32 (br m, 1H), 2.67-2.55 (br m, 2H), 2.21-2.15 (br m, 1H), 1.11 (d, 3H, J=6.9 Hz).

MS: m/z=378 [M+H]+

Example 16

Preparation of SR-MDOP (Compound [1])

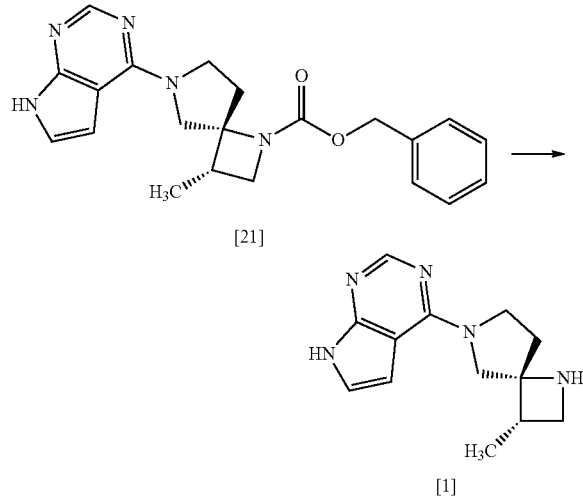

To a solution of SR-MDPZ [21] in tert-butanol (corresponding to 34.2 mmol) were added under nitrogen atmosphere ammonium formate (10.8 g, 171 mmol), water (60 mL) and 10% palladium-carbon (manufactured by Kawaken Fine Chemicals Co., Ltd., type M, 52.6% of water contained, 1.20 g). The reaction mixture was stirred at 40° C. for 13 hours, and then cooled to room temperature. The insoluble was filtered off. The reaction vessel and the insoluble were washed with tert-butanol (24 mL), and to the washings and the filtrate were added 8M aqueous sodium hydroxide solution (25.7 mL, 205 mmol) and sodium chloride (13.2 g). The reaction mixture was stirred at 50° C. for 2 hours, and then thereto was added toluene (84 mL) at room temperature, and the organic layer was separated. The resulting organic layer was washed with 20% brine (60 mL), and then thereto was added anhydrous sodium sulfate. The mixture was stirred, and then sodium sulfate was filtered. The filtrate residue was washed with a mixed solution (48 mL) of toluene:tert-butanol=1:1. The filtrate and the washings were collected and the solvent was removed under reduced pressure. To the concentrated residue was added toluene (60 mL), and the mixture was stirred at 50° C. for 2 hours. Then, the solvent was removed under reduced pressure. To the concentrated residue was further added toluene (60 mL), and the mixture was concentrated. To the concentrated residue was added toluene (48 mL), and the mixture was stirred at room temperature for 1 hour, and then under ice cooling for 1 hour. The precipitated solid was filtered, and the resulting solid was washed with toluene (24 mL). The resulting wet solid was dried under reduced pressure to give SR-MDOP [1] (7.07 g, 29.1 mmol) in the yield of 84.8%.

NMR and MS were measured for SR-MDOP that was synthesized in the same manner.

$^1$H-NMR (DMSO-d$_6$) δ: 11.57 (br s, 1H), 8.07 (s, 1H), 7.10 (d, 1H, J=3.2 Hz), 6.58 (d, 1H, J=3.2 Hz), 3.92-3.59 (br m, 4H), 3.49 (dd, 1H, J=8.3, 7.2 Hz), 2.93 (dd, 1H, J=7.2, 6.1 Hz), 2.61-2.53 (m, 2H), 2.12-2.01 (br m, 2H), 1.10 (d, 3H, J=6.9 Hz).

MS: m/z=244 [M+H]$^+$

Example 17

X-Ray Crystallography for Single Crystal

A single crystal of a co-crystal (Compound [3-1]) of Compound A (Compound [4]) with 3,5-dimethylpyrazole (2:1, molar ratio) was prepared and analyzed by X-ray crystallography.

(Method for Preparing a Single Crystal)

To a co-crystal of Compound A (Compound [4]) with 3,5-dimethylpyrazole (2:1, molar ratio) (10 mg) was added acetonitrile (1 mL), and the mixture was heated to 70° C. for 2 hours. The resulted solution was filtered through a membrane filter (PTFE, 13 mmφ). The filtrate was let stand at room temperature for 4 days to give a single crystal.

X-Ray diffraction data was measured with Beamline BL2S1 at Aichi Synchrotron Radiation Center, a radiation institution.

(Conditions for Measurement)
Wavelength: 0.74998 Å
Beam size: 100 μmφ)
Camera length: 90 mm
Offset: 70 mm (vertical direction)
Angle of oscillation: 2°
Angle range for measurement: 180°
Measurement temperature: 100K (−173.15° C.)

Results analyzed with the following data analysis program are shown in the following table.

(Data Analysis Program)
Data measurement, Processing of diffraction data: XDS
Crystal structure analysis: SHELX97
Structure refinement: Full-matrix least-squares on $F^2$

| | |
|---|---|
| Composition formula | $C_{37}H_{44}N_{14}O_2$ |
| Molecular weight | 716.86 |
| Measurement wavelength (Å) | 0.74998 |
| Crystalline system | Orthorhombic |
| Space group (Number) | $P2_12_12_1$ (#19) |
| a (Å) | 14.078 |
| b (Å) | 37.541 |
| c (Å) | 6.729 |
| α (°) | 90 |
| β (°) | 90 |
| γ (°) | 90 |
| Lattice volume (Å$^3$) | 3556.2 |
| Number of molecules Z | 8 (Compound A (Compound [4])), 4 (3,5-dimethylpyrazole) |
| Number of independent molecules Z' | 2 (Compound A (Compound [4])), 1 (3,5-dimethylpyrazole) |
| Calculated density ($\rho_{calc}$ g/cm$^3$) | 1.339 |
| Linear absorption coefficient (μ/mm$^{-1}$) | 0.089 |
| F (000) | 1520.0 |
| Crystal size (mm) | 0.01 × 0.03 × 0.01 |
| Measurement range for 2θ (°) | 3.08 to 56.48 |
| Exposure time (sec/°) | 4 |
| Measurement temperature (° C.) | −173.15 |
| Observed number of reflection | 24776 |
| Number of independent reflection | 8458 ($R_{int}$ = 0.1350) |
| Data/restraints/parameters | 8458/0/496 |
| Goodness of Fit on $F^2$ | 1.016 |
| Final $R_1$ indiexess [I > 2σ$_1$] | $R_1$ = 0.0765 |

-continued

| | |
|---|---|
| Final wR₂ indices [All reflections] | wR₂ = 0.1694 |
| Largest diff. peak/hole (e⁻Å⁻³) | 0.30/−0.25 |

Figure 5:
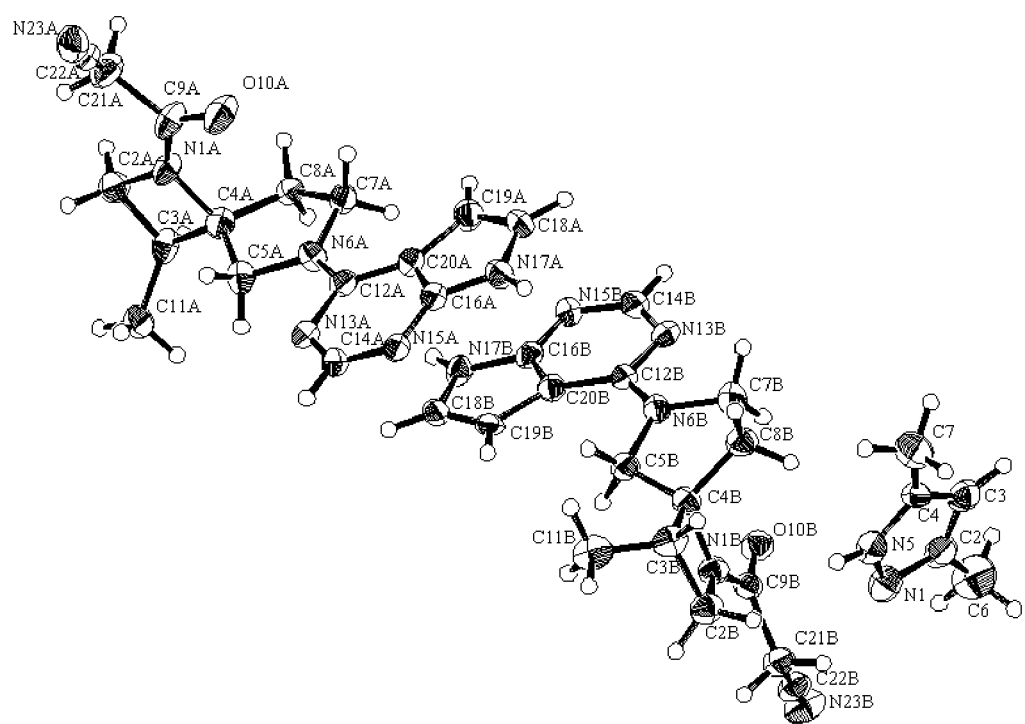
FIG. 5 shows an ORTEP drawing for a co-crystal (Compound [3-1]) of Compound A (Compound [4]) with 3,5-dimethylpyrazole (2:1, molar ratio).

The resulted single crystal was found to be a co-crystal according to a hydrogen bond between Compound A (Compound [4]) and 3,5-dimethylpyrazole. An ORTEP drawing for the resulted co-crystal of Compound A (Compound [4]) with 3,5-dimethylpyrazole (2:1, molar ratio) is shown in FIG. 5.

INDUSTRIAL APPLICABILITY

A co-crystal of Compound A (Compound [4]) with 3,5-dimethylpyrazole (e.g., Compound [3a]) in the present invention is useful for preparation of Compound A (Compound [4]). The present invention provides a process for stably preparing the co-crystal with a good chemical purity. The present invention also provides a process for stably preparing Compound A (Compound [4]) with a good chemical purity. Further, a process for preparation in the present invention is useful for an industrial production in large quantity because the co-crystal may be directly isolated from a reaction mixture.

The invention claimed is:

1. A co-crystal of 3-[(3S,4R)-3-methyl-6-(7H-pyrrolo[2,3-d]pyrimidin-4-yl)-1,6-diazaspiro[3.4]octan-1-yl]-3-oxo-propanenitrile with 3,5-dimethylpyrazole.

2. The co-crystal of claim 1, having the structure of formula [3a]

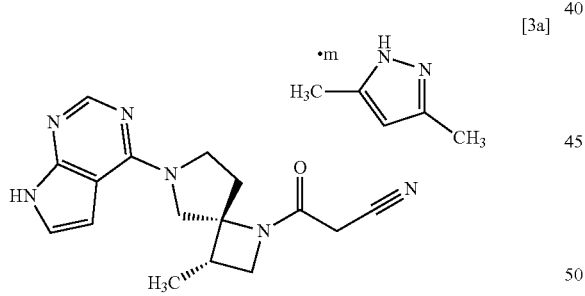

[3a]

wherein m is any number of 0.4 to 0.5.

3. The co-crystal of claim 2, wherein m is 0.5.

4. The co-crystal of claim 1, showing an extrapolated onset temperature of 172±5° C. in differential scanning calorimetry.

5. The co-crystal of claim 1, showing a X-ray powder diffraction pattern having at least one peak at 4.6°±0.2°, 18.6°±0.2° or 20.9°±0.2° of a diffraction angle (2θ)) measured by using CuKα radiation.

6. The co-crystal of claim 1, showing a X-ray powder diffraction pattern having at least one peak at 4.6°±0.2°, 12.6°±0.2°, 16.1°±0.2°, 18.6°±0.2° or 20.9°±0.2° of a diffraction angle (2θ)) measured by using CuKα radiation.

7. A process for preparing a compound of formula [4]

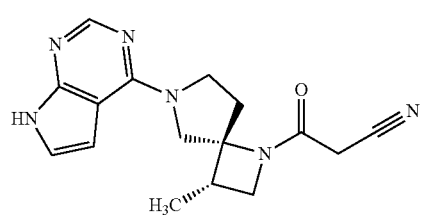

[4]

or its salt by employing the co-crystal of claim 1.

8. The process of claim 7, further comprising the step of reacting a compound of formula [1]

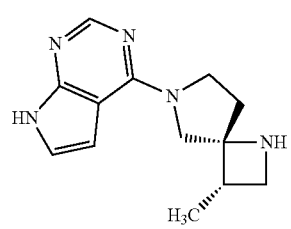

[1]

or its salt with a compound of formula [2]

[2]

to give a compound of formula [4] or its salt.

9. A process for purifying a compound of formula [4]

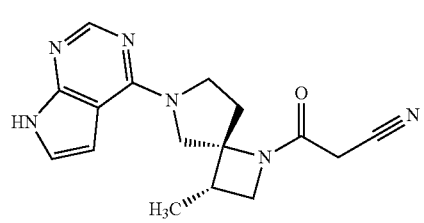

[4]

or its salt by employing the co-crystal of claim 1.

10. The process of claim 9, further comprising the step of reacting a compound of formula [1]

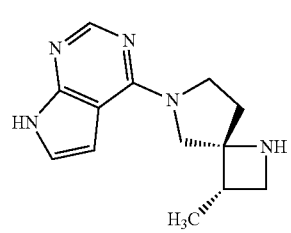

[1]

or its salt with a compound of formula [2]

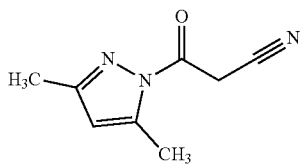

to give a compound of formula [4] or its salt.

11. A process for preparing a co-crystal having the structure of formula [3a]

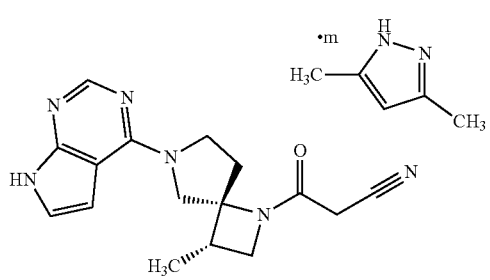

wherein m is any number of 0.4 to 0.5, comprising the step of reacting a compound of formula [1]

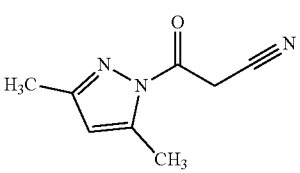

or its salt with a compound of formula [2]

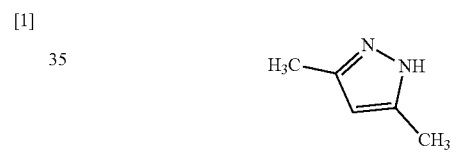

to give the co-crystal of formula [3a].

12. A process for preparing a co-crystal having the structure of formula [3a]

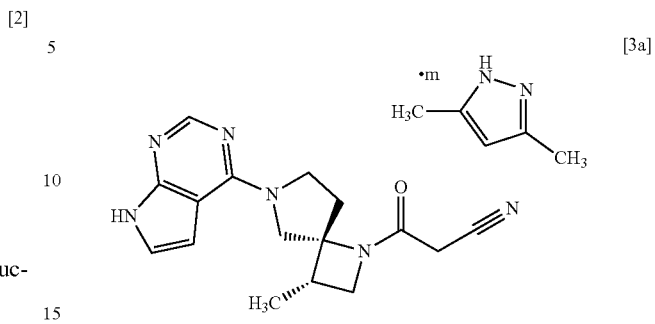

wherein m is any number of 0.4 to 0.5, comprising the step of reacting a compound of formula [4]

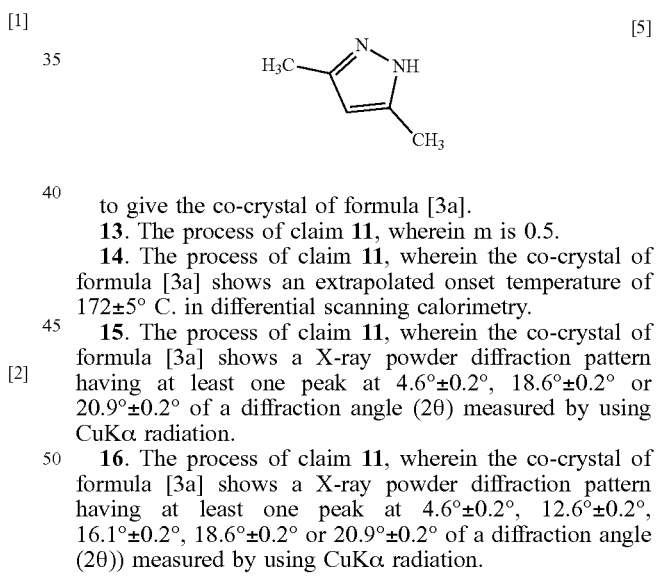

or its salt with a compound of formula [5]

to give the co-crystal of formula [3a].

13. The process of claim 11, wherein m is 0.5.

14. The process of claim 11, wherein the co-crystal of formula [3a] shows an extrapolated onset temperature of 172±5° C. in differential scanning calorimetry.

15. The process of claim 11, wherein the co-crystal of formula [3a] shows a X-ray powder diffraction pattern having at least one peak at 4.6°±0.2°, 18.6°±0.2° or 20.9°±0.2° of a diffraction angle (2θ) measured by using CuKα radiation.

16. The process of claim 11, wherein the co-crystal of formula [3a] shows a X-ray powder diffraction pattern having at least one peak at 4.6°±0.2°, 12.6°±0.2°, 16.1°±0.2°, 18.6°±0.2° or 20.9°±0.2° of a diffraction angle (2θ)) measured by using CuKα radiation.

* * * * *

UNITED STATES PATENT AND TRADEMARK OFFICE
CERTIFICATE OF CORRECTION

PATENT NO. : 11,312,728 B2
APPLICATION NO. : 16/470843
DATED : April 26, 2022
INVENTOR(S) : Shimazaki It is certified that error appears in the above-identified patent and that said Letters Patent is hereby corrected as shown below:

On the Title Page

Column 2, item (56) OTHER PUBLICATIONS
Line 1, delete "(Brittain," and insert -- Brittain, --.
Line 24, delete "Base" and insert -- Case --.

In the Claims

Column 35
Claim 5, Line 61, delete "($2\theta$))" and insert -- ($2\theta$) --.
Claim 6, Line 67, delete "($2\theta$))" and insert -- ($2\theta$) --.

Column 38
Claim 16, Line 54, delete "($2\theta$))" and insert -- ($2\theta$) --.

Signed and Sealed this
Second Day of August, 2022

Katherine Kelly Vidal
*Director of the United States Patent and Trademark Office*